US012605165B2

(12) United States Patent
Ouchi et al.

(10) Patent No.: US 12,605,165 B2
(45) Date of Patent: Apr. 21, 2026

(54) HEMOSTATIC DEVICE

(71) Applicant: TERUMO KABUSHIKI KAISHA, Tokyo (JP)

(72) Inventors: Tatsuya Ouchi, Fujinomiya (JP); Yuna Hidaka, Ibaraki (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 172 days.

(21) Appl. No.: 18/507,779

(22) Filed: Nov. 13, 2023

(65) Prior Publication Data

US 2024/0081832 A1 Mar. 14, 2024

Related U.S. Application Data

(63) Continuation of application No. PCT/JP2022/020040, filed on May 12, 2022.

(30) Foreign Application Priority Data

May 14, 2021 (JP) ................................. 2021-082265

(51) Int. Cl.
*A61B 17/135* (2006.01)
*A61B 17/12* (2006.01)

(52) U.S. Cl.
CPC .. *A61B 17/135* (2013.01); *A61B 2017/12004* (2013.01)

(58) Field of Classification Search
CPC ... A61B 17/12; A61B 17/132; A61B 17/1322; A61B 17/1325; A61B 17/1327;

(Continued)

(56) References Cited

U.S. PATENT DOCUMENTS

| | | | |
|---|---|---|---|
| 2001/0039399 A1* | 11/2001 | Bierman | ............... A61M 25/02 604/177 |
| 2018/0014832 A1 | 1/2018 | Lampropoulos et al. | |
| 2018/0070956 A1 | 3/2018 | Lampropoulos et al. | |

FOREIGN PATENT DOCUMENTS

| | | |
|---|---|---|
| JP | S5275096 U | 6/1977 |
| JP | 2019526299 A | 9/2019 |

(Continued)

OTHER PUBLICATIONS

English Translations of the International Search Report (Form PCT/ISA/210) and the Written Opinion of the International Searching Authority (Form PCT/ISA/237) issued Jul. 19, 2022, by the Japan Patent Office in corresponding International Application No. PCT/JP2022/020040. (5 pages).
International Search Report (PCT/ISA/210) with translation and Written Opinion (PCT/ISA/237) mailed on Jul. 19, 2022, by the Japan Patent Office as the International Searching Authority for International Application No. PCT/JP2022/020040. (9 pages).

*Primary Examiner* — Kankindi Rwego
(74) *Attorney, Agent, or Firm* — Buchanan Ingersoll & Rooney PC

(57) ABSTRACT

A hemostatic device is disclosed, which includes a tube fixing portion that is provided to a fixing member which fixes an inflatable member. The tube fixing portion includes a first member, a second member that is located closer to the inflatable member than is the first member, a slit portion, and a tube holding portion. A part of the first member is further away from the inflatable member than is the second member in a direction perpendicular to a virtual plane defined by the slit portion. A first distal-end surface includes a first region not facing a second distal-end surface, and a second region facing the second distal-end surface. A first curved portion has a first curved surface curved toward the second member and facing the second distal-end surface.

20 Claims, 14 Drawing Sheets

(58) Field of Classification Search
  CPC .............. A61B 17/135; A61B 17/1355; A61B
        2017/00243; A61B 2017/00557; A61B
        2017/00778; A61B 2017/00907; A61B
        2017/00955; A61B 2017/12004; A61B
        5/021; A61B 5/02141; A61B 5/022; A61F
        5/01; A61F 5/0118; A61F 5/05816; A61F
        5/05866; A61F 5/05875; A61F 5/012;
        A61F 5/013; A61F 5/30; A61F 5/32;
        A61F 5/34; A61F 2007/0001; A61F
        2007/0029; A61F 2007/0036; A61F
        2007/0037; A61F 2007/0038; A61H
        9/0078; A61H 9/0085; A61H 9/0092;
        A61H 1/006; A61M 25/02; A61M
        2025/0206; A61M 2025/024; A61M
        2025/0246
  USPC ................................. 606/201, 202, 203, 204
  See application file for complete search history.

(56)              References Cited

FOREIGN PATENT DOCUMENTS

WO        2019090104  A2      5/2019
WO        2019166913  A1      9/2019

* cited by examiner

<u>100</u>

HEMOSTATIC DEVICE

CROSS-REFERENCES TO RELATED APPLICATIONS

This application is a continuation of International Application No. PCT/JP2022/020040 filed on May 12, 2022, which claims priority to Japanese Application No. 2021-082265 filed on May 14, 2021, the entire content of both of which is incorporated herein by reference.

TECHNOLOGICAL FIELD

The present disclosure generally relates to a hemostatic device.

BACKGROUND DISCUSSION

As one of catheter procedures, a procedure is known in which various elongated medical devices are introduced into a blood vessel through a puncture site formed by puncturing the blood vessel of an arm or hand of a patient, and treatment or cure is performed on a lesion site.

For example, International Patent Application Publication No. WO2019/090104A discloses a hemostatic device for stopping bleeding at a puncture site formed to enable access to a blood vessel (including a distal radial artery) running in a hand.

The hemostatic device disclosed in International Patent Application Publication No. WO2019/090104 includes: an inflatable member that applies a compressive force to a puncture site formed in a hand of a patient; a fixing member that fixes a pressing member to the hand of the patient; an injection member including a port (connector portion) that can inject a fluid for inflating the inflatable member, and a tube portion that connects the connector portion to an inner cavity of the inflatable member; and a tube fixing portion that is located on the fixing member and can fix the tube portion.

An operator such as a doctor (hereinafter, referred to as an "operator") can help prevent the inflatable member from shifting from the puncture site formed in the hand of the patient by fixing the hemostatic device using bands in a state in which the inflatable member is disposed at the puncture site formed in the hand of the patient and a peripheral site of puncture site when stopping bleeding at the puncture site formed in the hand of the patient using the hemostatic device disclosed in International Patent Application Publication No. WO2019/090104.

The operator can reduce movement of the tube portion following movement of the hand of the patient by fixing the tube portion to the tube fixing portion.

However, the hemostatic device disclosed in International Patent Application Publication No. WO2019/090104 may have the following problems.

In the hemostatic device disclosed in International Patent Application Publication No. WO2019/090104, a groove for fixing the tube portion is formed in the tube fixing portion.

Therefore, when the operator attaches the tube portion to and detaches the tube portion from the tube fixing portion, the operator needs to deform (for example, elastically deform) the tube fixing portion in a direction in which the groove is widened by an external force applied to the tube portion.

At this time, the force required for the operator to deform the tube fixing portion in the direction in which the groove is widened is determined by a mechanical configuration of the tube fixing portion, but the configuration may not be designed in consideration of operability and convenience of the operator.

For example, when a force required for the operator to attach the tube portion to and detach the tube portion from the tube fixing portion is relatively large, the external force (the force applied by the operator) is transmitted to the inflatable member via the fixing member provided with the tube fixing portion, and thus the external force may be unintentionally applied to the puncture site.

When the external force is transmitted to the fixing member, the external force can be unintentionally transmitted to the inflatable member, and the inflatable member may shift from the puncture site formed in the hand of the patient accordingly.

SUMMARY

The present disclosure helps prevent an external force from being unintentionally applied to a puncture site due to transmission of the external force applied to a tube portion by an operator to an inflatable member via a tube fixing portion and a fixing member when the operator attaches the tube portion to and detaches the tube portion from the tube fixing portion in a state in which a hemostatic device is attached to a hand of a patient, and/or to help prevent the hemostatic device from shifting due to unintentional application of an external force to the inflatable member caused by transmission of the external force applied to the tube portion by the operator to the fixing member via the tube fixing portion.

A hemostatic device according to the disclosure includes: an inflatable member configured to compress a site where bleeding is to be stopped in a limb of a patient; a fixing member configured to secure or fix the inflatable member to the limb of the patient; an injection member including a connector portion configured to inject a fluid for inflating the inflatable member, and a tube portion connecting the connector portion to an inner cavity of the inflatable member; and a tube fixing portion located on the fixing member and configured to secure or fix the tube portion. The tube fixing portion includes a first member, a second member located closer to the inflatable member than is the first member and facing the first member, a slit portion formed between the first member and the second member and configured to allow insertion of the tube portion, and a tube holding portion surrounded by the first member, the second member, and the slit portion and configured to hold the tube portion. The first member includes a first portion, a first curved portion curved toward the second member, and a first distal-end surface located at a distal end of the first curved portion. The second member includes a second portion, a second curved portion curved toward the first member, and a second distal-end surface located at a distal end of the second curved portion and facing the first distal-end surface across the slit portion. A part of the first member is further away from the inflatable member than is the second member in a direction perpendicular to a virtual plane defined by the slit portion. The first distal-end surface includes a first region not facing the second distal-end surface across the slit portion and a second region facing the second distal-end surface across the slit portion. The first curved portion has a first curved surface curved toward the second member. The first curved surface faces the second distal-end surface across the tube holding portion.

In the hemostatic device configured as described above, by providing a height difference between the first member

3 and the second member forming the tube fixing portion, a region where a distal-end surface (first distal-end surface) of the first member and a distal-end surface (second distal-end surface) of the second member face each other across the slit portion is reduced.

Therefore, when an operator pushes the tube portion into the tube fixing portion (inserts into the tube fixing portion), the first member is deformed in a direction in which the slit portion is widened, and then the second member is deformed.

Accordingly, the hemostatic device can reduce a force required for the operator to insert the tube portion into the tube fixing portion in a state of being attached to a hand of the patient.

The first member of the hemostatic device includes a first curved surface at a position facing the second distal-end surface of the second member across the tube holding portion.

Therefore, when the operator separates the tube portion from the tube fixing portion (removes from the tube fixing portion), the tube portion is moved from the tube holding portion toward the slit portion with the first curved surface as a guide surface.

Accordingly, the hemostatic device can reduce a force required for the operator to remove the tube portion from the tube fixing portion.

A tube fixing portion that is provided on a fixing member configured to fix an inflatable member of a hemostatic device to a patient is disclosed, the tube fixing portion includes: a first member, a second member located closer to the inflatable member than the first member and facing the first member; a slit portion formed between the first member and the second member and configured to allow insertion of a tube portion configured to be connected to an inner cavity of the inflatable member; a tube holding portion surrounded by the first member, the second member, and the slit portion and configured to hold the tube portion; the first member includes a first portion, a first curved portion curved toward the second member, and a first distal-end surface located at a distal end of the first curved portion; and the second member includes a second portion, a second curved portion curved toward the first member, and a second distal-end surface located at a distal end of the second curved portion and facing the first distal-end surface across the slit portion.

A method is disclosed for attaching a hemostatic device to a site where bleeding is to be stopped in a limb of a patient, the method includes: positioning an inflatable member fixed on a support member of the hemostatic device over the site to where the bleeding is to be stopped in the limb of the patient; securing the inflatable member of the hemostatic device to the limb of the patient with a plurality of bands connected to the support member; and fixing a tube portion of an injection member to the support member using a tube fixing portion located on the support member and configured to fix the tube portion, the tube fixing portion including a first member, a second member located closer to the inflatable member than is the first member and facing the first member, a slit portion formed between the first member and the second member and configured to allow insertion of the tube portion, and a tube holding portion surrounded by the first member, the second member, and the slit portion and configured to hold the tube portion.

As described above, since the hemostatic device can reduce a force required for the operator to attach the tube portion to and detach the tube portion from the tube fixing portion in a state of being attached to the hand of the patient, it is possible to prevent an external force from being unintentionally applied to the puncture site and/or to prevent the hemostatic device from shifting due to unintentional application of an external force to the inflatable member.

DETAILED DESCRIPTION

Figure 1:
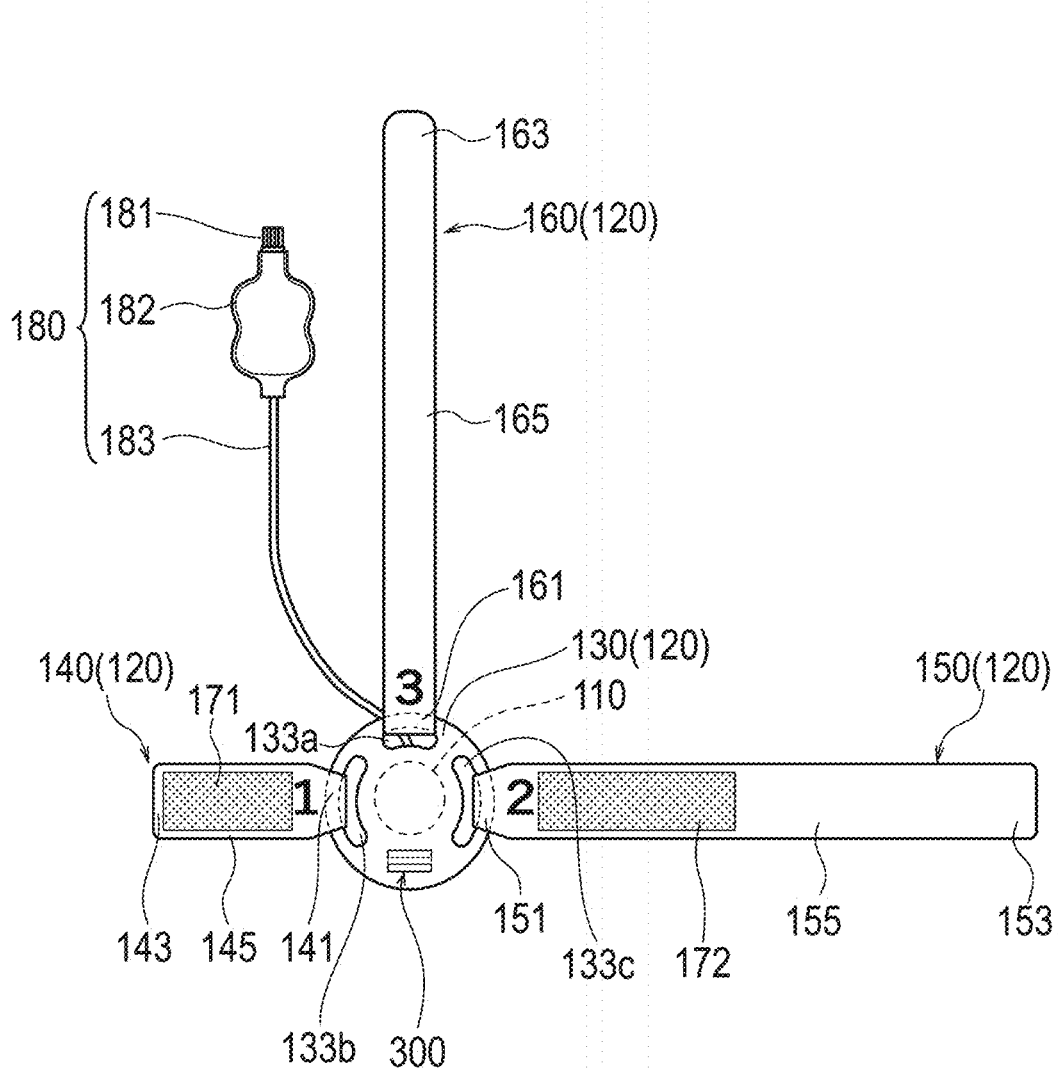
FIG. 1 is a plan view showing a hemostatic device according to an embodiment, as viewed from an outer surface side of each band.

Set forth below with reference to the accompanying drawings is a detailed description of embodiments of a hemostatic device.

The following description does not limit the technical scope and meaning of terms described in the claims.

Dimensional ratios in the drawings are exaggerated for convenience of illustration, and may be different from actual ratios.

FIGS. 1 to 10 are views showing a hemostatic device 100 according to the present embodiment, and FIGS. 11 to 16 are views showing a usage example of the hemostatic device 100.

For example, as shown in FIGS. 11 and 14 to 16, the hemostatic device 100 can be used to stop bleeding at a puncture site (for example, each of puncture sites p1 and p2 to be described later) formed in a hand H located on a distal side (finger side) with respect to a forearm A of a patient when a sheath tube of an introducer 200 that is indwelled in the puncture site is removed.

A specific position of the puncture site where bleeding is to be stopped by the hemostatic device 100 is not particularly limited, and the following first puncture site p1 is exemplified in the present embodiment.

Figure 11:
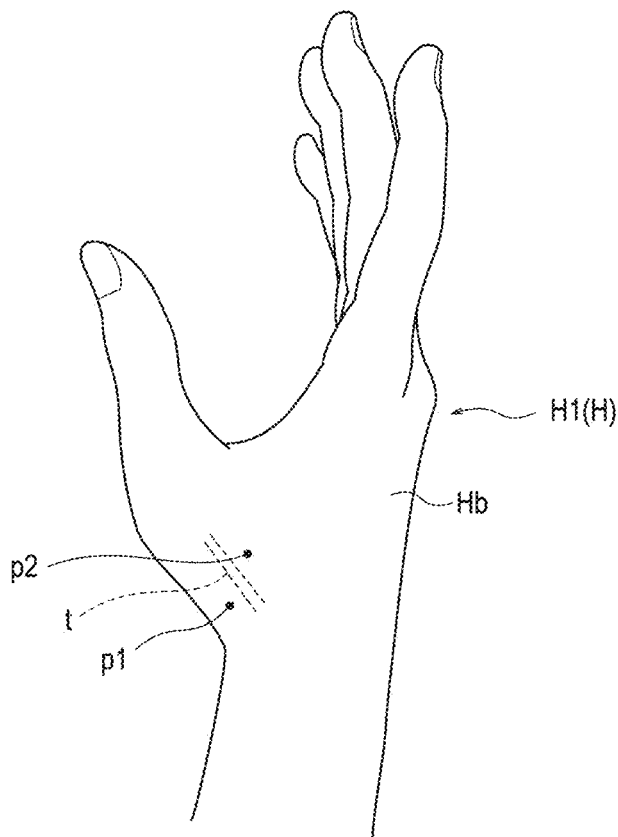
FIG. 11 is a view showing a hand (right hand) of a patient to whom the hemostatic device is to be used.

As shown in FIG. 11, the first puncture site p1 is a puncture site formed in an artery B (hereinafter also referred to as a "blood vessel B") located in a snuff box of a palmar artery running on a dorsal side Hb of a right hand H1 (hand H) located on a distal side with respect to the forearm A of the patient.

The snuff box is a hollow of the hand located near a radius when the patient spreads a thumb of the hand H.

As shown in FIG. 11, the second puncture site p2 is a puncture site formed in a distal radial artery located on a distal side with respect to the snuff box of the palmar artery running on the dorsal side Hb of the right hand H1 of the patient. The second puncture site p2 is located on a distal side of the right hand H1 with respect to the first puncture site p1 with reference to an extensor pollicis longus tendon t located at the dorsal side Hb of the right hand H1 of the patient.

Hereinafter, the hemostatic device 100 will be described.

Hemostatic Device

As shown in FIGS. 1 to 4 and FIGS. 14 to 16, the hemostatic device 100 can include: an inflatable member 110 that compresses the first puncture site p1 formed on the right hand H1 of the patient; a fixing member 120 that can fix the inflatable member 110 to the right hand H1 of the patient; an injection member 180 including a connector portion 181 that can inject a fluid for inflating the inflatable member 110, and a tube portion 183 that connects the connector portion 181 to an inner cavity 113 of the inflatable member 110; and a tube fixing portion 300 that is located on the fixing member 120 and is configured to be capable of fixing the tube portion 183.

Inflatable Member

Figure 6:
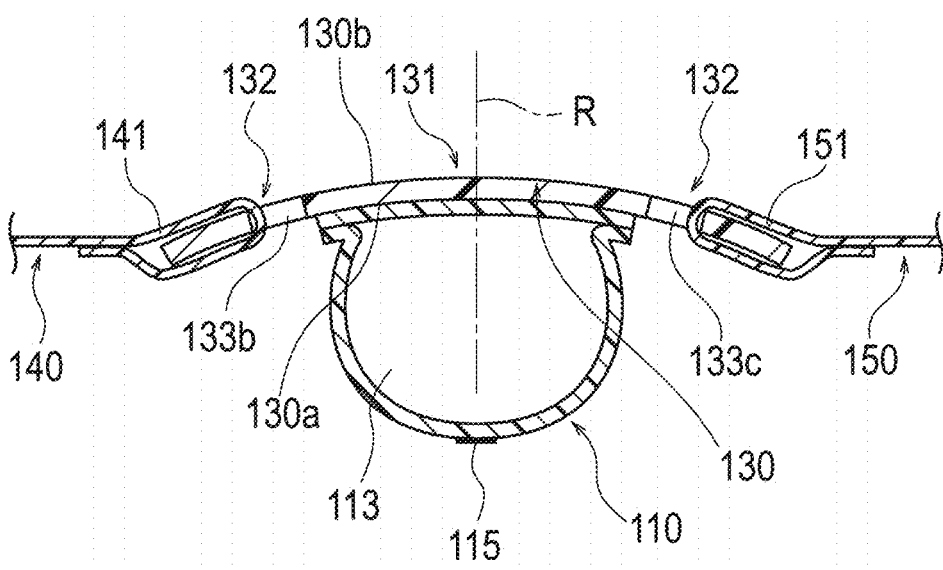
FIG. 6 is a cross-sectional view of the hemostatic device taken along an arrow VIA-VIA shown in FIG. 5, showing a state in which an inflatable member is inflated.
Figure 7:
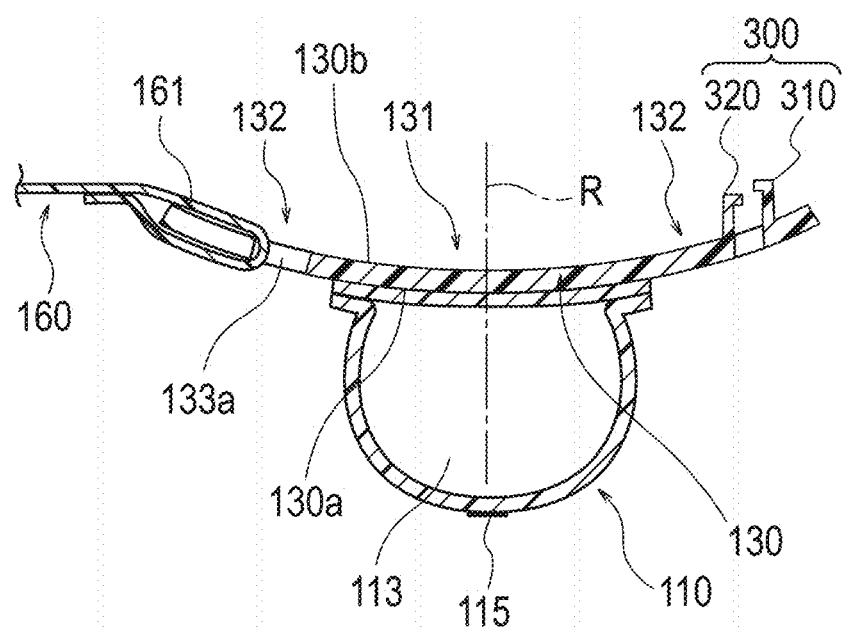
FIG. 7 is a cross-sectional view of the hemostatic device taken along an arrow VIIA-VIIA shown in FIG. 5, showing a state in which the inflatable member is inflated.

As shown in FIGS. 6 and 7, the inflatable member 110 can be implemented, for example, by a single balloon having the inner cavity 113 partitioned by a film member.

The inflatable member 110 can be formed by, for example, joining edge portions of two sheet-shaped film members formed in a substantially rectangular shape in a state in which the inner cavity 113 is defined between the two sheet-shaped film members.

The inflatable member 110 may be formed of, for example, a single film-shaped member formed in a bag shape so as to have an inner cavity.

The inflatable member 110 is inflated when a fluid such as air is supplied to the inner cavity 113, and is contracted when the fluid supplied to the inner cavity 113 is discharged.

FIGS. 6 and 7 show cross-sectional views when the fluid is supplied to the inflatable member 110 and the inflatable member 110 is inflated.

The film member forming the inflatable member 110 can be made of, for example, a resin material having a predetermined thickness. The tube portion 183 (see FIGS. 1 and 2) to be described later is connected to the inner cavity 113 of the inflatable member 110.

A material of the film member forming the inflatable member 110 is not particularly limited, and examples of the material of the film member forming the inflatable member 110 can include polyolefins such as polyvinyl chloride, polyethylene, polypropylene, polybutadiene, and ethylene-vinyl acetate copolymer (EVA), polyesters such as polyethylene terephthalate (PET) and polybutylene terephthalate (PBT), various thermoplastic elastomers such as polyvinylidene chloride, silicone, polyurethane, polyamide elastomer, polyurethane elastomer, and polyester elastomer, nylon, nylon elastomer, and any combination thereof (blend resin, polymer alloy, laminate, and the like).

As shown in FIGS. 6, 7, 15, and 16, the inflatable member 110 is disposed on an inner surface 130a side of a support member 130 provided on the fixing member 120.

An inner surface 130a of the support member 130 is a surface disposed on a surface side of the hand H of the patient when the hemostatic device 100 is attached to the hand H of the patient. An outer surface 130b of the support member 130 is a surface opposite to the inner surface 130a.

The inflatable member 110 can be directly connected to the inner surface 130a of the support member 130. The inflatable member 110 and the support member 130 can be connected by, for example, fusion bonding or adhesion.

The inflatable member 110 may be connected to the inner surface 130a of the support member 130 via another member.

The inflatable member 110 may be, for example, formed of a single film-shaped member defining an inner cavity between the inflatable member 110 and the inner surface 130a of the support member 130. For example, the inflatable member 110 may be configured such that one film-shaped member is directly connected to the inner surface 130a of the support member 130, and an inner cavity is defined between the inner surface 130a of the support member 130 and the one film-shaped member.

The inflatable member 110 has a circular shape in a plan view shown in FIGS. 1 to 5.

However, a shape of the inflatable member 110 in the plan view is not limited to the circular shape.

Cross-sectional shapes of the inflatable member 110 before and after inflation, a specific structure of the inflatable member 110, and the like are not particularly limited.

As shown in FIGS. 2, 4, 6, 7, 15, and 16, a marker 115 that aligns the inflatable member 110 with the first puncture site p1 is disposed on the inflatable member 110.

The marker 115 is disposed on an outer surface of a surface of the inflatable member 110 that is opposite to a surface on which the support member 130 is disposed (a surface disposed on the surface side of the hand H of the patient when the hemostatic device 100 is attached to the hand H of the patient).

A specific arrangement position of the marker 115 is not particularly limited as long as the marker 115 is disposed on the inflatable member 110. For example, the marker 115 may be disposed on an inner surface of the surface of the inflatable member 110 that is opposite to the surface on which the support member 130 is disposed (the surface disposed on the surface side of the hand H of the patient when the hemostatic device 100 is attached to the hand H of the patient).

Figure 5:
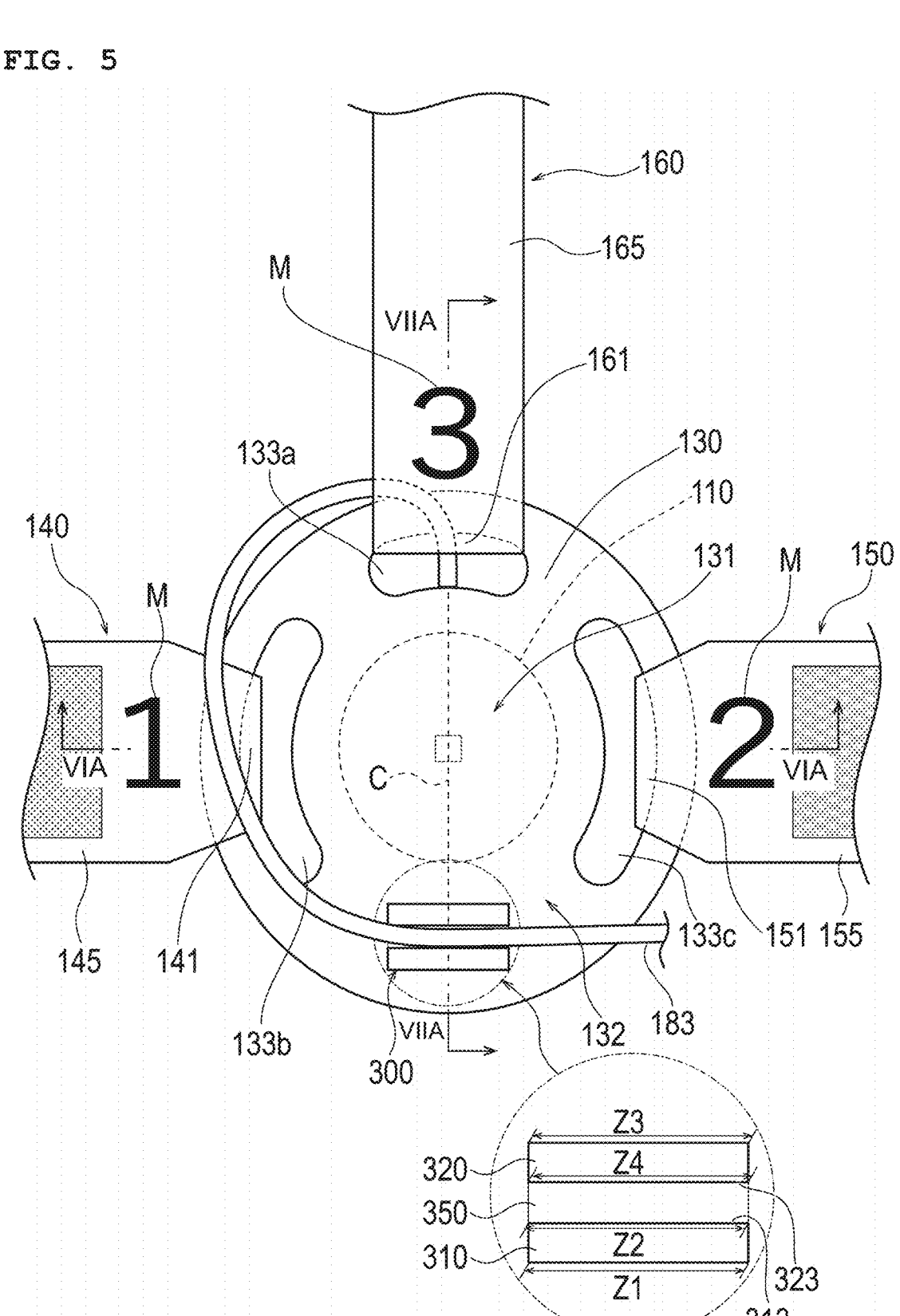
FIG. 5 is an enlarged plan view of a part of the hemostatic device as viewed from the outer surface side of each band.

As shown in FIG. 5, the marker 115 is disposed at a substantially central position of the inflatable member 110 in a plane direction. The marker 115 overlaps (extends over) a substantially central position of the support member 130 in a plane direction. The plane direction of the inflatable member 110 and the plane direction of the support member 130 refer to a direction in which the support member 130 (inflatable member 110) extends in the plan view shown in FIG. 5.

The marker 115 can be formed of, for example, a rectangular marker in which the entire marker 115 is colored. The shape, the size, the color, the formation method, the position, and the like of the marker 115 are not particularly limited. For example, the marker 115 may be provided on the support member 130.

Fixing Member

As shown in FIG. 1, the fixing member 120 includes the support member 130, and a plurality of bands 140, 150, and 160 that are connectable to the support member 130 and are to be wrapped around the hand H of the patient.

Support Member

As shown in FIGS. 3-7, the support member 130 includes a first region 131 where the inflatable member 110 is disposed, and a second region 132 that is located outside the first region 131 and is connectable to the first band 140, the second band 150, and the third band 160.

The support member 130 has a circular shape in the plan view shown in FIG. 5.

The first region 131 is a region that overlaps (or extends over) the inflatable member 110 in the plan view shown in FIG. 5. The second region 132 is a region located outside the first region 131 in the plan view shown in FIG. 5.

The first region 131 can be arbitrarily defined based on the outer shape and size of the inflatable member 110 disposed on the support member 130. The second region 132 can be defined based on a relative positional relationship with the first region 131. Therefore, the first region 131 and the second region 132 can be appropriately changed according to the outer shape and size of the inflatable member 110 disposed on the support member 130.

Figure 8:
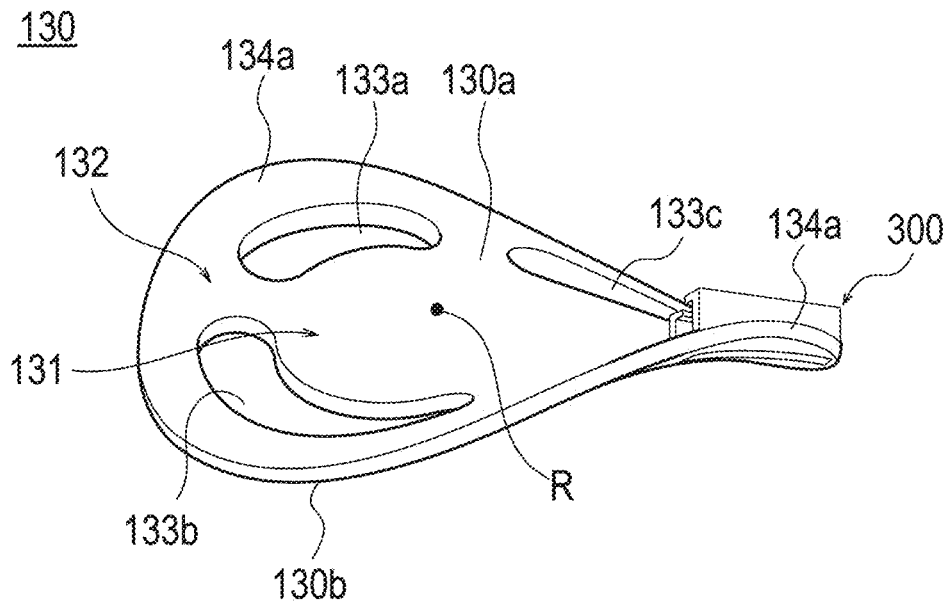
FIG. 8 is a perspective view showing a support member.

As shown in FIGS. 6-8, a center point R, which is a center when the first band 140 and the second band 150 slide along second holes 133b and 133c, is located in the first region 131. The center point R is located at the substantially central position of the support member 130 in the plane direction. Therefore, as shown in FIGS. 6 and 7, the center point R is located at a position overlapping the marker 115 when projected onto the inflatable member 110.

As shown in FIGS. 5-9, the second region 132 has a first hole 133a and the pair of second holes 133b and 133c facing each other with the inflatable member 110 interposed between the pair of second holes 133b and 133c.

As shown in FIG. 5, when the hemostatic device 100 is attached to the hand H of the patient, the first hole 133a is disposed on the distal side (fingertip side) of the hand H with respect to the inflatable member 110.

As shown in FIG. 5, the second hole 133b and the second hole 133c are formed with the inflatable member 110 interposed between the pair of second holes 133b and 133c in a direction intersecting a straight line connecting the first hole 133a and the inflatable member 110 (a straight line connecting the first hole 133a and the tube fixing portion 300. The straight line is shown as a virtual line C in FIG. 5).

Figure 3:
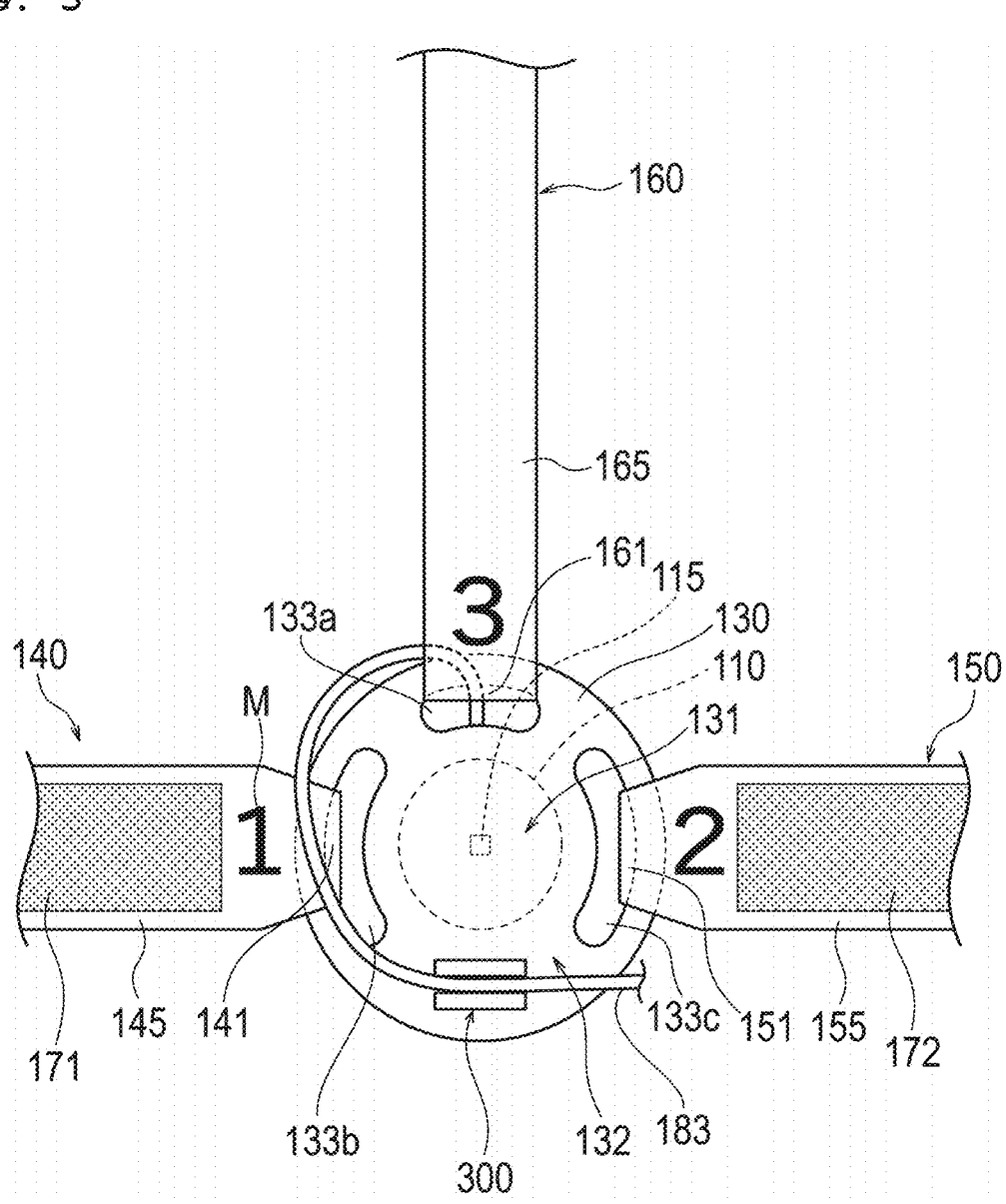
FIG. 3 is an enlarged plan view of a part of the hemostatic device as viewed from the outer surface side of each band.
Figure 4:
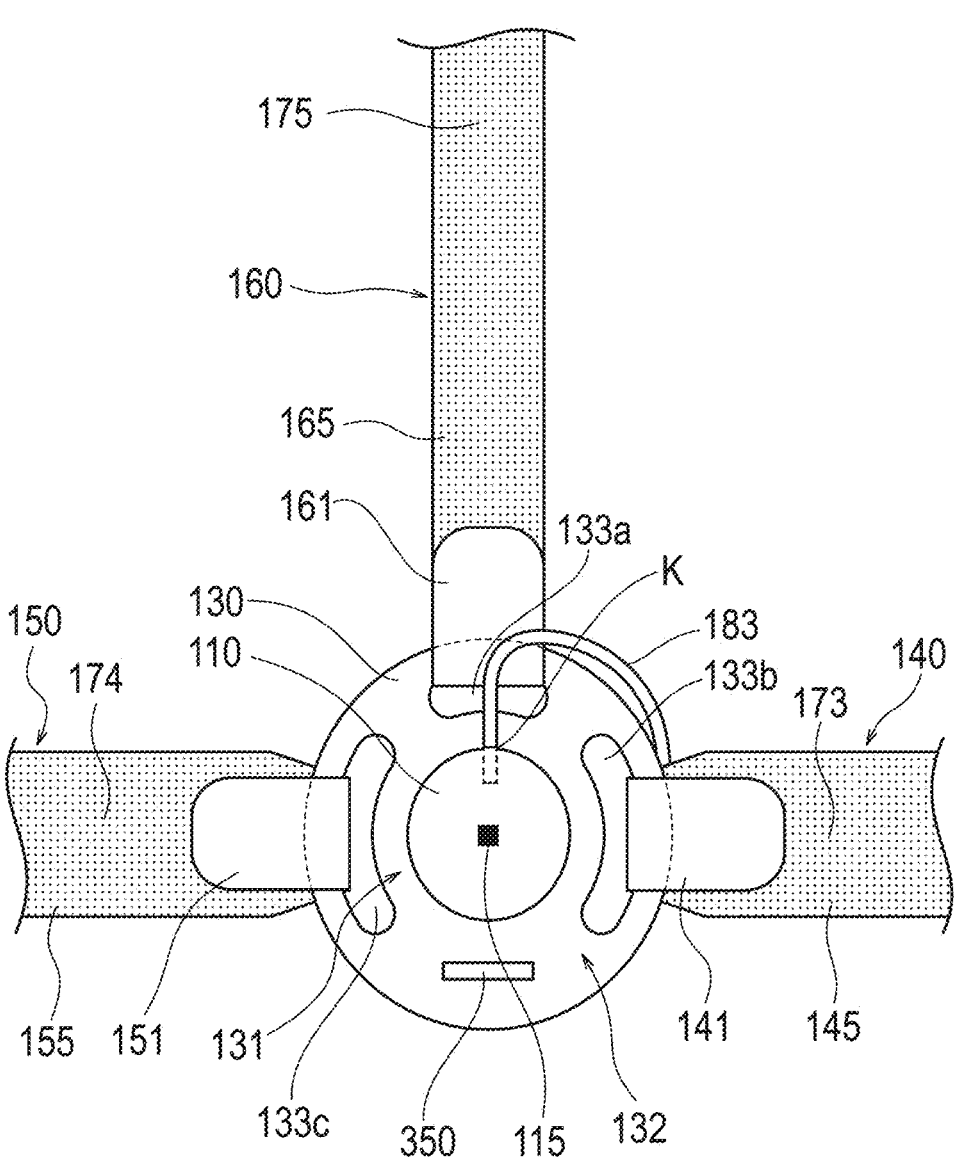
FIG. 4 is an enlarged plan view of a part of the hemostatic device as viewed from the inner surface side of each band.

As shown in FIGS. 3-5, the holes 133a, 133b, and 133c are formed on a virtual circle along an outer shape of the support member 130.

As shown in FIGS. 3-7, the first band 140 is connected to the second hole 133b.

The second band 150 is connected to the second hole 133c.

The third band 160 is connected to the first hole 133a.

As shown in FIG. 5, a width of one end portion 141 of the first band 140 is smaller than a hole length of the second hole 133b. Therefore, as shown in FIG. 8, the first band 140 is slidable around the inflatable member 110 in the second region 132 about the center point R of the support member 130 in a state in which the one end portion 141 of the first band 140 is connected to the second hole 133b.

As shown in FIG. 5, a width of one end portion 151 of the second band 150 is smaller than a hole length of the second hole 133c.

Therefore, as shown in FIG. 8, the second band 150 is slidable around the inflatable member 110 in the second region 132 about the center point R in a state in which the one end portion 151 of the second band 150 is connected to the second hole 133c.

An angle (slidable range) at which the first band 140 and the second band 150 are slidable around the inflatable member 110 about the center point R is not particularly limited, and may be set to, for example, 1° to 75°.

As shown in FIG. 5, a width of one end portion 161 of the third band 160 is substantially the same as a hole length of the first hole 133a. Therefore, the third band 160 can be restricted from sliding about the center point R in a state in which the one end portion 161 of the third band 160 is connected to the first hole 133a.

Figure 9:
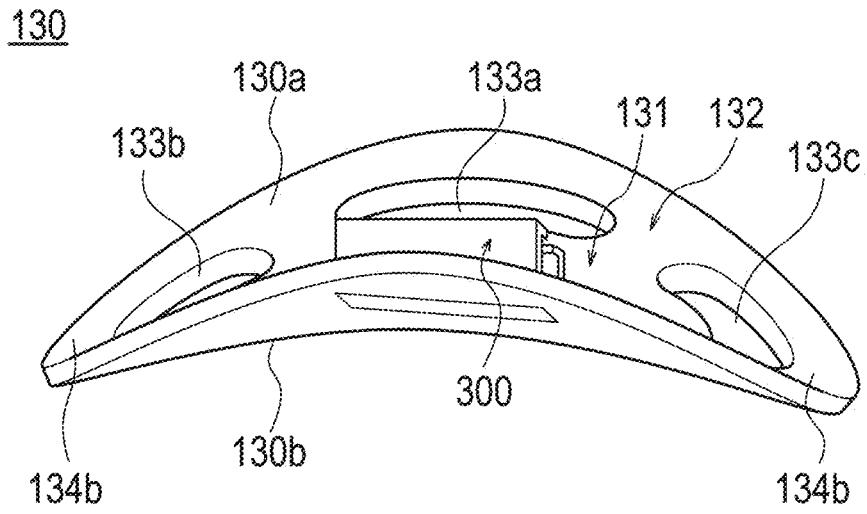
FIG. 9 is a perspective view showing the support member.

As shown in FIGS. 8 and 9, first curved regions 134a each curved in a convex shape away from the inflatable member 110 (an upper side in FIGS. 6 and 7) are formed in portions where the first hole 133a and the tube fixing portion 300 are disposed in the second region 132 of the support member 130.

As shown in FIGS. 8 and 9, second curved regions 134b each curved in a convex shape toward the inflatable member 110 (a lower side in FIGS. 6 and 7) are formed in portions where the second holes 133b and 133c are formed in the second region 132 of the support member 130.

The support member 130 is made of a more rigid material than the bands 140, 150, and 160.

Examples of the constituent material of the support member 130 having the rigidity as described above include acrylic resin, polyvinyl chloride (in particular, rigid polyvinyl chloride), polyolefin such as polyethylene, polypropylene, and polybutadiene, polystyrene, poly-(4-methylpentene-1), polycarbonate, ABS resin, polymethyl methacrylate (PMMA), polyacetal, polyacrylate, polyacrylonitrile, polyvinylidene fluoride, ionomer, acrylonitrile-butadiene-styrene copolymer, and polyethylene terephthalate (PET).

In each of the inflatable member 110 and the support member 130, portions overlapping each other in the plan view shown in FIGS. 3 and 4 can be transparent. In a case where the inflatable member 110 and the support member 130 are configured as described above, as shown in FIGS. 12, 13, and 14, when the hemostatic device 100 is attached to the right hand H1 of the patient, an operator can rather easily visually check positions of the marker 115 and/or the first puncture site p1 via the inflatable member 110 and the support member 130. The term "transparent" can include colored transparent, colorless transparent, and translucent.

Band

As shown in FIGS. 1, 2, 3, and 4, the first band 140 includes the one end portion 141 that is connectable to the second hole 133b of the support member 130, the other end portion 143 that is free and not connected to the support member 130, and a portion (or body portion) 145 that extends between the one end portion 141 and the other end portion 143.

As shown in FIGS. 1-5, the second band 150 includes the one end portion 151 that is connectable to the second hole 133c of the support member 130, the other end portion 153 that is free and not connected to the support member 130, and a portion (or body portion) 155 that extends between the one end portion 151 and the other end portion 153.

The first band 140 extends from the support member 130 in a predetermined first direction. The second band 150 extends from the support member 130 in a predetermined second direction different from the first direction.

9

Figure 12:
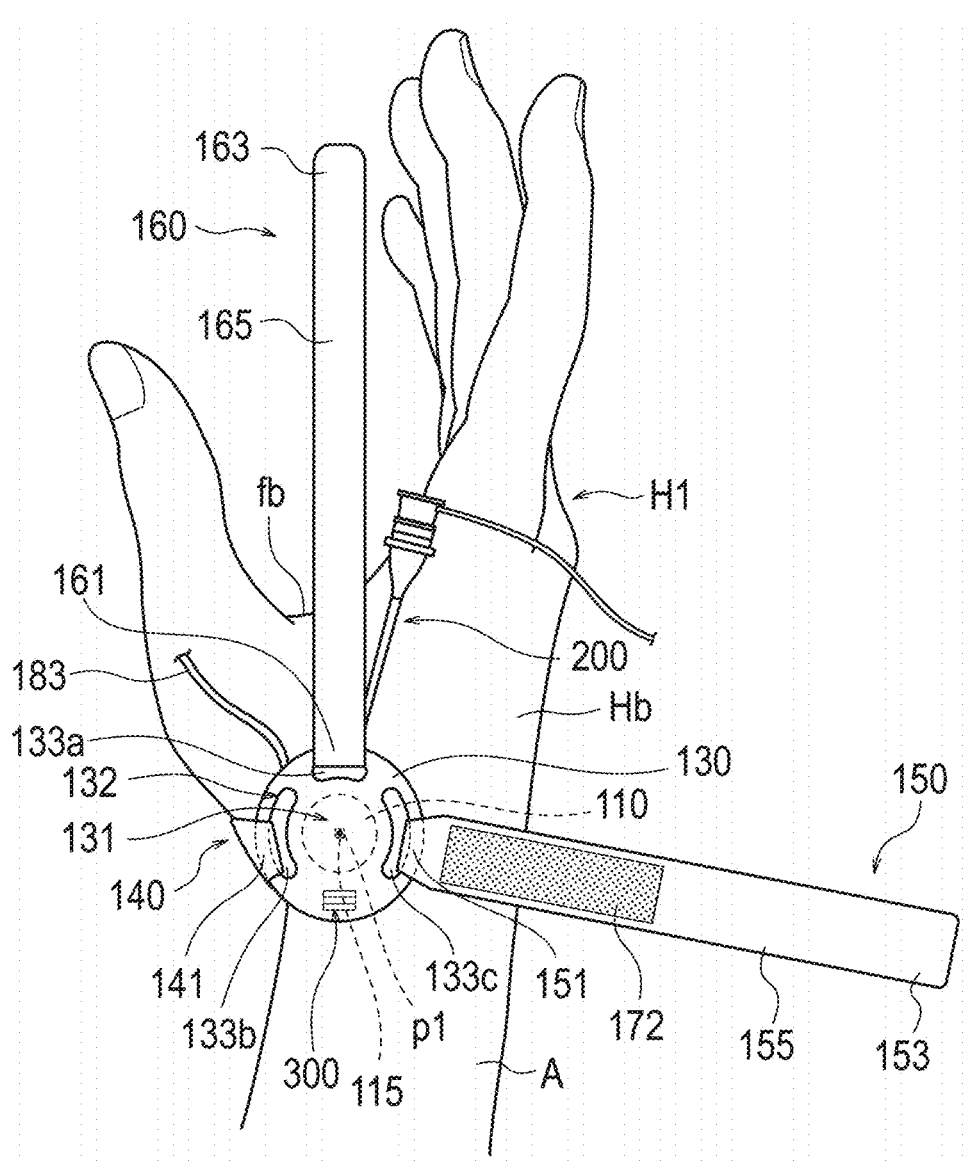
FIG. 12 is a view schematically showing a usage example of the hemostatic device.
Figure 13:
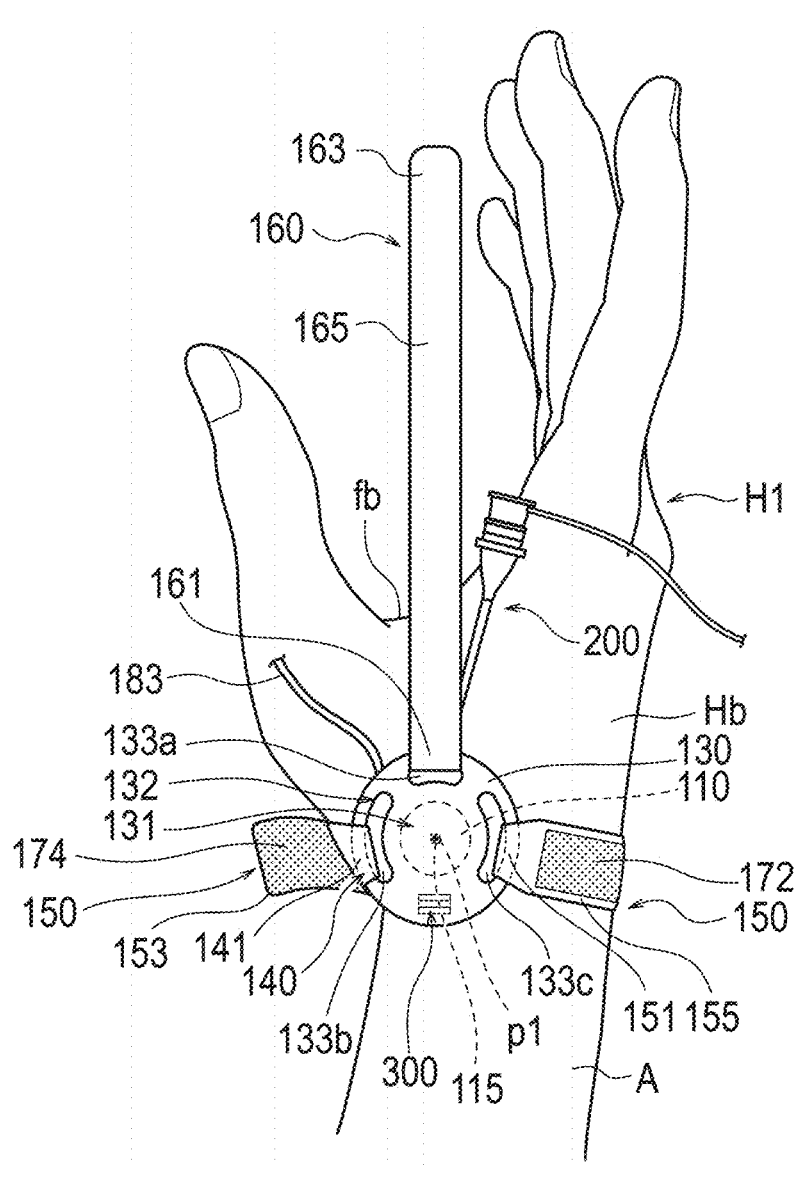
FIG. 13 is a view schematically showing the usage example of the hemostatic device.
Figure 14:
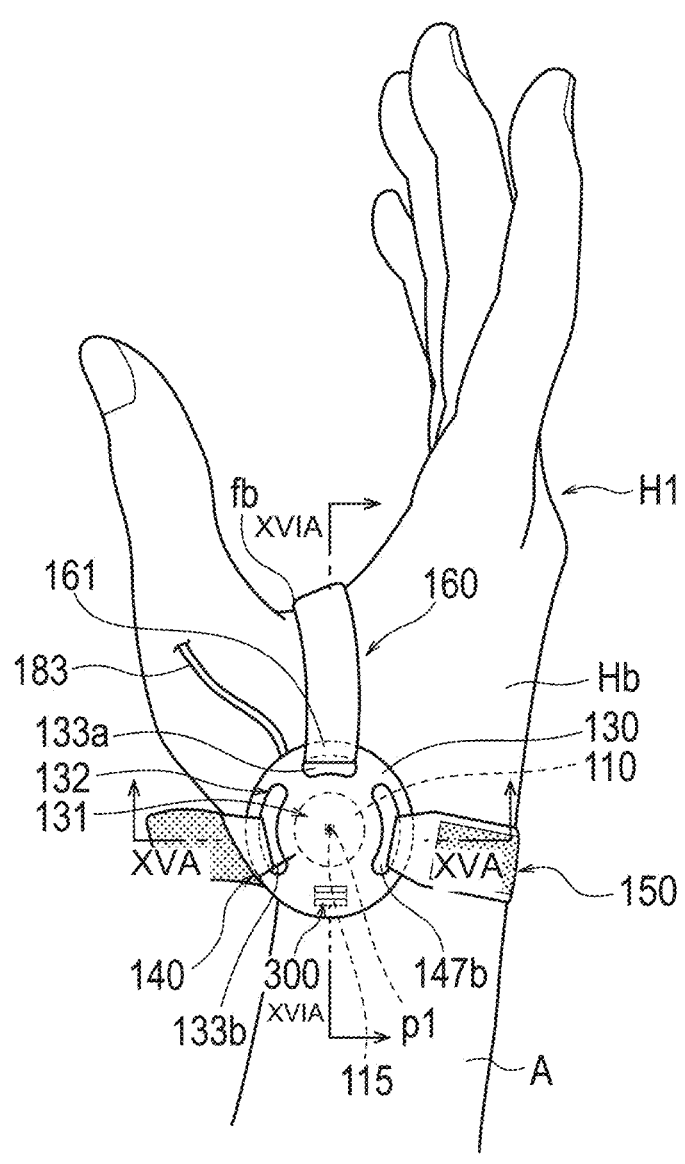
FIG. 14 is a view schematically showing the usage example of the hemostatic device.

As shown in FIGS. 12, 13, and 14, when the hemostatic device 100 is attached to the right hand H1 of the patient, the first band 140 and the second band 150 can be wrapped around an outer periphery of the right hand H1.

As shown in FIGS. 1-5, the third band 160 includes the one end portion 161 that is connectable to the first hole 133a of the support member 130, the other end portion 163 that is free and not connected to the support member 130, and a portion (body portion) 165 that extends between the one end portion 161 and the other end portion 163.

The third band 160 extends from the support member 130 in a third direction different from the first direction in which the first band 140 extends and the second direction in which the second band 150 extends.

As shown in FIG. 14, the third band 160 can be hooked on an inter-finger portion fb located between the thumb and the forefinger of the right hand H1 of the patient in a state in which the inflatable member 110 is disposed at the first puncture site p1.

The one end portions 141, 151, and 161 of the bands 140, 150, and 160 can be inserted into and rolled (or wrapped) around the holes 133a, 133b, and 133c of the support member 130, respectively. Note that a structure for connecting the one end portions 141, 151, and 161 of the bands 140, 150, and 160 to the support member 130 is not particularly limited. For example, a member (for example, a hook-and-loop fastener) capable of holding and releasing a state of being rolled (or wrapped) around each of the holes 133a, 133b, and 133c of the support member 130 can be disposed at respective one end portions 141, 151 and 161.

The one end portions 141, 151, and 161 of the bands 140, 150, and 160 are provided with symbols M (including, for example, figures and characters) for identifying the individual bands 140, 150, and 160.

In the present embodiment, the one end portion 141 of the first band 140, the one end portion 151 of the second band 150, and the one end portion 161 of the third band 160 are respectively provided with numbers "1", "2", and "3".

The numbers provided on the bands 140, 150, and 160 correspond to an order of rolling the bands 140, 150, and 160 when the operator attaches the hemostatic device 100 to the right hand H1 of the patient.

Therefore, the operator can attach the bands 140, 150, and 160 to the right hand H1 of the patient in a correct order by visually recognizing the symbols M.

The size, the color, the formation method, the position, and the like of the symbol M are not particularly limited.

A constituent material of each of the bands 140, 150, and 160 is not particularly limited, and may be, for example, vinyl chloride resin, amide resin, amide elastomer resin, polyurethane resin, or polyester resin. The shape, the length, the thickness, and the like of each of the bands 140, 150, and 160 are not particularly limited.

As shown in FIGS. 1-4, the hemostatic device 100 can include five fixing sites, namely a first fixing site 171, a second fixing site 172, a third fixing site 173, a fourth fixing site 174, and a fifth fixing site 175.

As shown in FIGS. 1 and 3, the first fixing site 171 is disposed on an outer surface of the first band 140. The second fixing site 172 is disposed on an outer surface of the second band 150.

Figure 2:
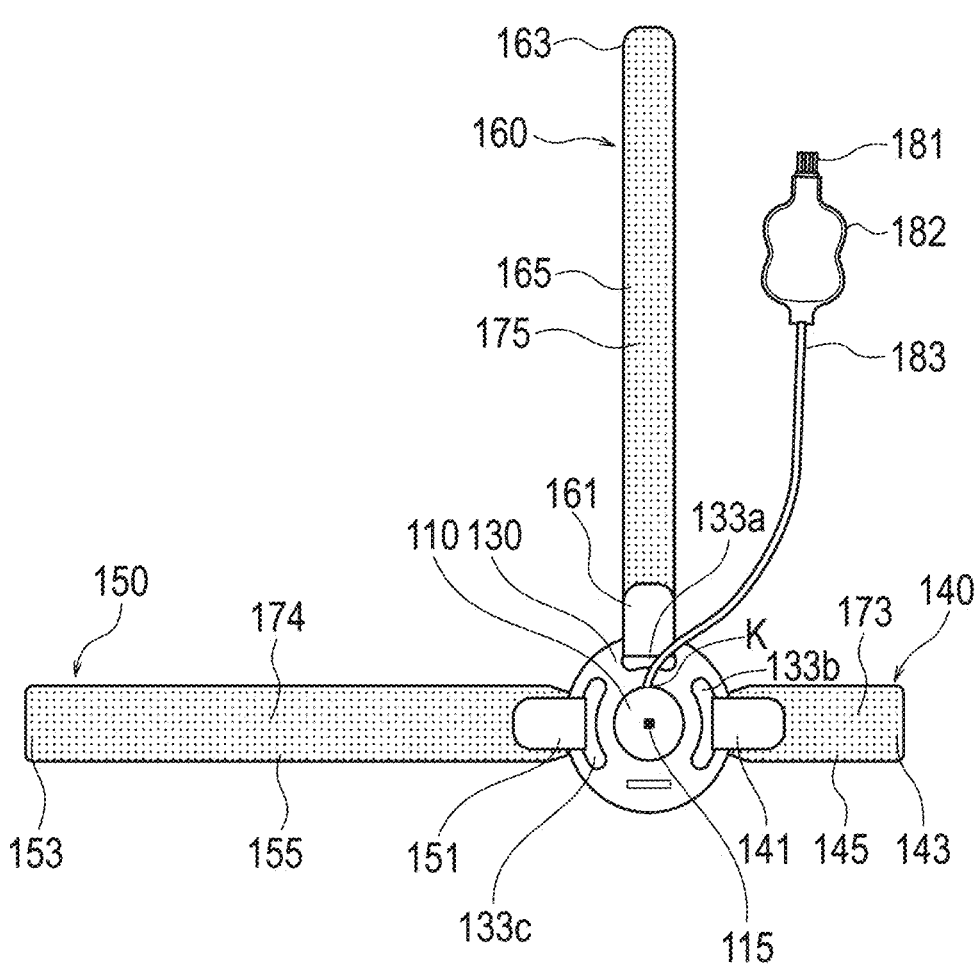
FIG. 2 is a plan view showing the hemostatic device according to the present embodiment, as viewed from an inner surface side of each band.

As shown in FIGS. 2 and 4, the third fixing site 173 is disposed on an inner surface of the first band 140. The fourth fixing site 174 is disposed on an inner surface of the second band 150. The fifth fixing site 175 is disposed on an inner surface of the third band 160.

The "inner surface" of each of the bands 140, 150, and 160 is a surface disposed on a surface side of the patient when the hemostatic device 100 is attached to the patient, and the "outer surface" of each of the bands 140, 150, and 160 is a surface located on a side opposite to the inner surface.

The first fixing site 171 and the second fixing site 172 are each formed of a male side of the hook-and-loop fastener.

The third fixing site 173, the fourth fixing site 174, and the fifth fixing site 175 are each formed of a female side of the hook-and-loop fastener.

The hook-and-loop fastener in this specification is a fastener that can be attached to and detached from a surface, such as Magic Tape® and Velcro®.

The fixing sites 171, 172, 174, and 175 are used to connect the bands 140, 150, and 160 to one another in a state in which the hemostatic device 100 is attached to the right hand H1 of the patient.

The one end portions 141, 151, and 161 corresponding to the fixing sites 173, 174, and 175 are used to connect the bands 140, 150, and 160 to the support member 130.

The specific structures of the fixing sites 171, 172, 174, and 175 are not limited as long as the support member 130 can be fixed to the right hand H1 of the patient.

For example, arrangement of a part of the fixing sites can be omitted and positions of the fixing sites in the bands 140, 150, and 160 can be changed as desired.

When each of the fixing sites 171, 172, 173, 174, and 175 is formed of the hook-and-loop fastener, a configuration may be such that the male and female sides of the hook-and-loop fastener are interchanged.

Each of the fixing sites 171, 172, 173, 174, and 175 may be formed of, for example, a snap, a button, a clip, a coupling mechanism including a frame portion having a hole and an engaged portion including a protrusion engageable with the frame portion, or the like.

Injection Member

As shown in FIGS. 1 and 2, the injection member 180 includes the connector portion 181 that can inject a fluid for inflating the inflatable member 110, and the tube portion 183 that connects the connector portion 181 to the inner cavity 113 of the inflatable member 110.

The connector portion 181 can have a built-in check valve.

A syringe, for example, can be connected to the connector portion 181.

A cushioning member 182 having an inflatable space is disposed between the connector portion 181 and the inflatable member 110.

The cushioning member 182 can be formed of a flexible bag-shaped member having a space defined in the flexible bag-shaped member.

The cushioning member 182 may be provided with an arrow-shaped marker indicating an insertion direction of the syringe into the connector portion 181.

The connector portion 181 is connected to one end side of the cushioning member 182.

An inner cavity of the connector portion 181 communicates with the space of the cushioning member 182.

However, while the check valve built in the connector portion 181 is closed, communication between the inner cavity of the connector portion 181 and the space of the cushioning member 182 is blocked.

The flexible tube portion 183 is connected to the other end side of the cushioning member 182.

An inner cavity of the tube portion 183 communicates with the space of the cushioning member 182.

The tube portion 183 is connected to the inflatable member 110 at the other end portion opposite to one end portion connected to the cushioning member 182.

The inner cavity of the tube portion 183 communicates with the inner cavity 113 of the inflatable member 110.

When inflating the inflatable member 110, the operator inserts, for example, a front tube portion of the syringe into the connector portion 181 to open the check valve.

The operator injects air in the syringe into the inner cavity 113 of the inflatable member 110 by pushing a plunger of the syringe in a state in which the check valve of the connector portion 181 is opened.

When the air is injected into the inner cavity 113 of the inflatable member 110, the inflatable member 110 is inflated.

When the inflatable member 110 is inflated, the cushioning member 182 communicating with the inner cavity 113 of the inflatable member 110 via the tube portion 183 is inflated.

The operator can relatively easily recognize that the inflatable member 110 is inflated without air leakage by visually checking inflation of the cushioning member 182.

When contracting the inflatable member 110, the operator inserts the front tube portion of the syringe into the connector portion 181 and pulls the plunger of the syringe.

The operator can discharge the air in the inner cavity 113 of the inflatable member 110 to the syringe by performing the above-described operation.

The connector portion 181, the cushioning member 182, and the tube portion 183 may be prepared and provided in a state of being connected to the inflatable member 110, or in a state of being separated from the inflatable member 110.

Tube Fixing Portion

Figure 10:
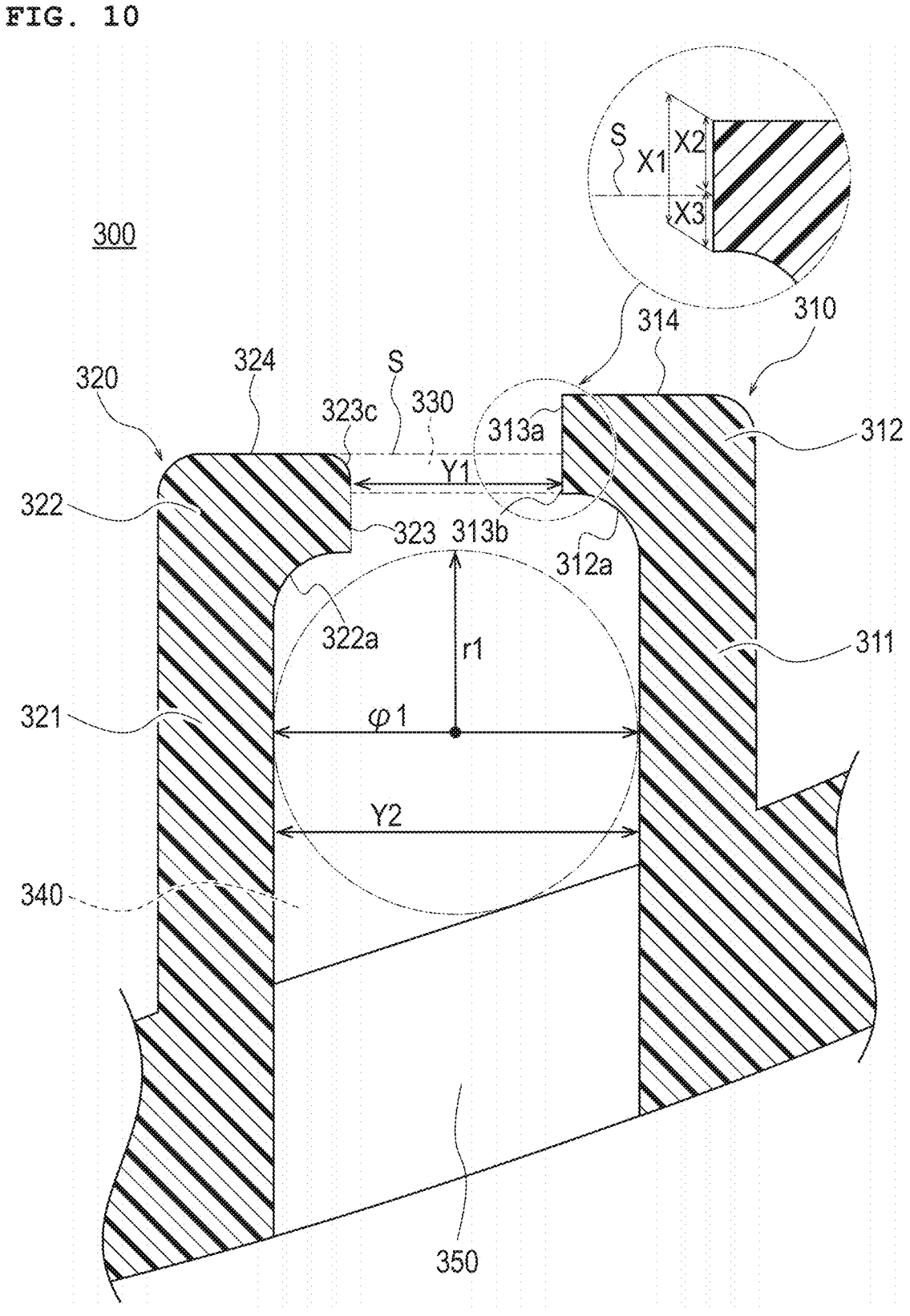
FIG. 10 is a cross-sectional view showing a tube fixing portion, and is an enlarged view of a part of FIG. 7.

As shown in FIGS. 5 and 10, the tube fixing portion 300 includes a first member 310, a second member 320 that is located closer to the inflatable member 110 than is the first member 310 and faces the first member 310, a slit portion 330 that is formed between the first member 310 and the second member 320 and allows insertion of the tube portion 183, and a tube holding portion 340 that is surrounded by the first member 310, the second member 320, and the slit portion 330 and holds the tube portion 183.

As shown in FIG. 10, the first member 310 includes a first portion (first body portion) 311, a first curved portion 312 that is curved toward the second member 320, and a first distal-end surface 313 that is located at a distal end of the first curved portion 312.

As shown in FIG. 10, the second member 320 includes a second portion (second body portion) 321, a second curved portion 322 that is curved toward the first member 310, and a second distal-end surface 323 that is located at a distal end of the second curved portion 322 and faces the first distal-end surface 313 across the slit portion 330.

As shown in FIG. 10, the first portion 311 and the second member 320 extend from the support member 130 in a direction substantially perpendicular to the plane direction of the support member 130 and away from the support member 130. As shown in an enlarged view of the tube fixing portion 300 in FIG. 5, a width Z1 of the first portion 311 (here, the "width" is a length in a left-right direction in FIG. 5) is set to be the same value as a width Z2 of the first distal-end surface 313, and a width Z3 of the second portion 321 is set to be the same value as a width Z4 of the second distal-end surface 323.

The width Z1 of the first portion 311, the width Z2 of the first distal-end surface 313, the width Z3 of the second portion 321, and the width Z4 of the second distal-end surface 323 are a length of the tube fixing portion 300 in a left-right direction in FIG. 1.

As shown in FIG. 10, a width Y1 of the slit portion 330 formed between the first curved portion 312 and the second curved portion 322 (here, the "width" is a length in a left-right direction in FIG. 10) is less than a width Y2 of the tube holding portion 340 and less than a diameter φ1 of the tube portion 183.

Therefore, the hemostatic device 100 can help prevent the tube portion 183 inserted into the tube holding portion 340 from being unintentionally removed from the tube fixing portion 300.

The width Y2 of the tube holding portion 340 is preferably equal to the diameter φ1 of the tube portion 183.

With this configuration, the hemostatic device 100 can help prevent the tube portion 183 from moving in the left-right direction in FIG. 5 in the tube holding portion 340.

A height of the tube holding portion 340 (here, the "height" is a length in an upper-lower direction in FIG. 10) is preferably equal to the diameter φ1 of the tube portion 183.

With this configuration, the hemostatic device 100 can help prevent the tube portion 183 from moving in the upper-lower direction in FIG. 10 in the tube holding portion 340.

Therefore, the hemostatic device 100 can help prevent the tube portion 183 inserted into the tube holding portion 340 from being unintentionally removed from the tube fixing portion 300.

The width Y1 of the slit portion 330 and the width Y2 of the tube holding portion 340 are a length of the tube fixing portion 300 in an upper-lower direction in FIG. 1.

A part of the first member 310 (a part of the first curved portion 312) is further away from the inflatable member 110 than is the second member 320 in a direction perpendicular to a virtual plane S defined by the slit portion 330, and the first distal-end surface 313 includes a first region 313a that does not face the second distal-end surface 323 across the slit portion 330, and a second region 313b that facing the second distal-end surface 323 across the slit portion 330.

As shown in FIG. 10, the virtual plane S defined by the slit portion 330 here refers to a plane that passes through an upper end surface 324 of the second member 320 and extends toward the first member 310.

For example, as shown in FIG. 10, the virtual plane S is a plane that passes through the upper end surface 324 of the second member 320 and extends perpendicularly toward the first member 310.

The hemostatic device 100 has a height difference between the first member 310 and the second member 320 with reference to the virtual plane S.

An upper end surface 314 of the first member 310 is higher than the upper end surface 324 of the second member 320 (away from the inflatable member 110).

The hemostatic device 100 is configured so that a region where the first distal-end surface 313 and the second distal-end surface 323 face each other across the slit portion 330 in a height direction of the tube fixing portion 300 (the upper-lower direction in FIG. 10) is reduced. The region is a region where the first distal-end surface 313 and the second distal-end surface 323 overlap each other in a direction orthogonal to the upper-lower direction in FIG. 10.

Therefore, in the hemostatic device 100, when the operator pushes the tube portion 183 into the tube fixing portion 300 (inserts the tube portion 183 into the tube fixing portion 300), the first member 310 can be deformed in a direction in which the slit portion 330 is widened by an external force applied to the tube portion 183, and then the second member 320 can be deformed in the direction in which the slit portion 330 is widened in a state of maintaining deformation of the first member 310.

Accordingly, the hemostatic device 100 can reduce a force required for the operator to insert the tube portion 183 into the tube fixing portion 300 in a state of being attached to the right hand H1 of the patient, and the operator can rather easily insert the tube portion 183 into the tube fixing portion 300.

In the hemostatic device 100 (the support member 130), a hole 350 is formed between the first member 310 and the second member 320 as shown in FIGS. 4, 5, and 10.

As shown in FIG. 10, the hole 350 is a through hole located between the first member 310 and the second member 320 and penetrating the support member 130 between the inner surface 130a and the outer surface 130b of the support member 130.

Note that a position of the hole 350 is not particularly limited as long as the position of the hole 350 is between the first member 310 and the second member 320 in the plan view shown in FIG. 5.

The support member 130 has the hole 350 between the first member 310 and the second member 320. Accordingly, in the hemostatic device 100, when an external force (a force pressing the tube portion 183 in the left-right direction in FIG. 5, for example, a force pressing the tube portion 183 from a left side to a right side in FIG. 5 or a force pressing the tube portion 183 from the right side to the left side in FIG. 5) is applied to the tube portion 183 in a state in which the tube portion 183 is inserted into the tube holding portion 340, a part of the tube portion 183 enters the hole 350, whereby deformation of the tube portion 183 between a connection portion K and the tube fixing portion 300 and movement of tube portion 183 in a direction away from the outer surface 130b of the support member 130 can be reduced.

Therefore, in the hemostatic device 100, even when the external force is applied to the tube portion 183 in a state in which the tube portion 183 is inserted into the tube holding portion 340, deformation of the tube portion 183 between the connection portion K and the tube fixing portion 300 can be reduced, and the operator or the like can be prevented from being caught by the deformed tube portion 183. In addition, in the hemostatic device 100, when the external force (the force pressing the tube portion 183 from the left side to the right side in FIG. 5) is applied to the tube portion 183 in a state in which the tube portion 183 is inserted into the tube holding portion 340, a part of the tube portion 183 enters the hole 350, whereby the tube portion 183 can be prevented from moving from the left side to the right side in FIG. 5, and the connector portion 181 and the cushioning member 182 can be prevented from sliding in a direction away from the tube fixing portion 300.

Therefore, in the hemostatic device 100, when the external force (the force pressing the tube portion 183 from the left side to the right side in FIG. 5) is applied to the tube portion 183 in a state in which the tube portion 183 is inserted into the tube holding portion 340, sliding of the connector portion 181 and the cushioning member 182 from the left side to the right side in FIG. 5 can be reduced, and the connector portion 181 and the cushioning member 182 can be prevented from being caught by a member located around the patient such as a bed.

The hole 350 functions as a hole for removing a mold when molding the first member 310 and the second member 320.

Therefore, in the hemostatic device 100, the number of molds when molding the support member 130 that is integrally formed with the tube fixing portion 300 can be reduced, and a manufacturing cost can be reduced.

A vertical width of the hole 350 (here, the "vertical width" is a length in an upper-lower direction in FIG. 5 and a length in the left-right direction in FIG. 10) can be the width Y2 of the tube holding portion 340, for example.

The vertical width of the hole 350 is preferably equal to or greater than the diameter φ1 of the tube portion 183.

Accordingly, in the hemostatic device 100, when the external force (the force pressing the tube portion 183 in the left-right direction in FIG. 5) is applied to the tube portion 183 in a state in which the tube portion 183 is inserted into the tube holding portion 340, a part of the tube portion 183 can easily enter the hole 350.

A lateral width of the hole 350 (here, the "lateral width" is a length in the left-right direction in FIG. 5) can be the width Z1 of the first portion 311 or the width Z3 of the second portion 321, for example.

As shown in FIG. 10, the first curved portion 312 has a first curved surface 312a that is curved toward the second member 320.

The first curved surface 312a is formed at a position facing the second distal-end surface 323 across the tube holding portion 340.

Therefore, in the hemostatic device 100, when the operator separates the tube portion 183 from the tube fixing portion 300 (removes the tube portion 183 from the tube fixing portion 300), the tube portion 183 is moved from the tube holding portion 340 toward the slit portion 330 with the first curved surface 312a as a guide surface.

Accordingly, the hemostatic device 100 can reduce a force required for the operator to remove the tube portion 183 from the tube fixing portion 300 in a state of being attached to the right hand H1 of the patient, and the operator can rather easily remove the tube portion 183 from the tube fixing portion 300.

As shown in FIG. 10, the second curved portion 322 has a second curved surface 322a that is curved toward the first member 310.

In the hemostatic device 100, when the operator removes the tube portion 183 from the tube fixing portion 300, the tube portion 183 fixed to the tube fixing portion 300 is moved along the first curved surface 312a and/or the second curved surface 322a, whereby the tube portion 183 can be easily directed to the slit portion 330.

Accordingly, it is relatively easier for the operator to remove the tube portion 183 from the tube fixing portion 300.

A thickness of a distal portion of each of the first curved portion 312 and the second curved portion 322 (that is, a length X1 of the first distal-end surface 313 obtained by adding a length X2 of the first region 313a and a length X3 of the second region 313b of the first distal-end surface 313, or a length of the second distal-end surface 323. Here, the "length" is a length in the upper-lower direction in the enlarged view of the first distal-end surface 313 in FIG. 10) is not particularly limited, and can be set to any thickness with little risk of breakage when the tube fixing portion 300 is formed stably and the operator attaches the tube portion 183 to and detaches the tube portion 183 from the tube fixing portion 300.

As described above, the tube fixing portion 300 is configured such that the region where the first distal-end surface 313 and the second distal-end surface 323 face each other across the slit portion 330 in the height direction of the tube fixing portion 300 (the upper-lower direction in FIG. 10) can be reduced.

Accordingly, the tube fixing portion 300 can be designed such that distal portions of the first curved portion 312 and the second curved portion 322 have a relatively large thicknesses while reducing a force required for the operator to attach the tube portion 183 to and detach the tube portion 183 from the tube fixing portion 300.

However, the length X3 of the second region 313b of the first distal-end surface 313 is preferably less than a radius r1 of the tube portion 183.

With such a configuration, when the operator inserts the tube portion 183 into the tube fixing portion 300, the hemostatic device 100 can reduce an amount of work required for the operator to move the tube portion 183 from the slit portion 330 toward the tube holding portion 340 (referring to an amount obtained by multiplying an external force applied to the tube portion 183 by the operator by a moving distance of the tube portion 183. Here, the "distance" is a moving distance along the first distal-end surface 313 and a moving distance along the second distal-end surface 323 facing each other across the slit portion 330).

Therefore, the hemostatic device 100 can reduce a force with which the operator pushes the tube portion 183 from the slit portion 330 toward the tube holding portion 340, and the operator can easily insert the tube portion 183 into the tube fixing portion 300.

As shown in FIG. 10, the second distal-end surface 323 includes a curved surface portion 323c at a position facing the first distal-end surface 313 across the slit portion 330.

Since the curved surface portion 323c is formed between the upper end surface 324 and the second distal-end surface 323 of the second member 320 adjacent to the slit portion 330, the hemostatic device 100 guides a moving direction of the tube portion 183 to the curved surface portion 323c when inserting the tube portion 183 into the tube fixing portion 300, and facilitates the tube portion 183 held by the tube holding portion 340 to be directed to the slit portion 330.

Therefore, the hemostatic device 100 can reduce the force required for the operator to insert the tube portion 183 into the tube fixing portion 300 in a state of being attached to the right hand H1 of the patient, and the operator can rather easily insert the tube portion 183 into the tube fixing portion 300.

As described above, the hemostatic device 100 can reduce a force required for the operator to attach the tube portion 183 to and detach the tube portion 183 from the tube fixing portion 300 in a state of being attached to the right hand H1 of the patient. Therefore, in the hemostatic device 100, it is possible to help prevent an external force from being unintentionally applied to the first puncture site p1, and/or to help prevent the hemostatic device 100 from shifting due to unintentional application of an external force to the inflatable member 110.

The tube fixing portion 300 can be made of a material more rigid than a material forming the tube portion 183.

As shown in FIG. 3, the tube fixing portion 300 is located on the outer surface 130b of the support member 130, and the support member 130 is made of a material that is more rigid than the bands 140, 150, and 160.

Therefore, the operator can rather easily perform an operation of attaching the tube portion 183 to and detaching the tube portion 183 from the tube fixing portion 300 in a state in which the hemostatic device 100 is attached to the right hand H1 of the patient.

Since the tube fixing portion 300 is made of a material that is more rigid than the tube portion 183, the first portion 311 and the second member 320 are less likely to be deformed by an unintentionally applied force, and the tube portion 183 held by the tube fixing portion 300 can be prevented from unintentionally being removed from the tube fixing portion 300.

Since the tube fixing portion 300 is provided on the support member 130 made of the relatively rigid material, the hemostatic device 100 can be prevented from shifting due to unintentional application of the external force to the inflatable member 110 connected to the support member 130.

As shown in FIG. 3, when the tube fixing portion 300 is located on the outer surface 130b of the support member 130 outside the inflatable member 110, the hemostatic device 100 can be reliably prevented from shifting due to unintentional application of the external force to the inflatable member 110 connected to the support member 130.

Note that a method for forming the tube fixing portion 300 is not particularly limited, and as shown in FIG. 3, the tube fixing portion 300 can be formed integrally with the support member 130, and can be made of the same constituent material as the support member 130.

A position of the tube fixing portion 300 is not limited as long as the tube fixing portion 300 is provided at a position where the tube portion 183 is relatively easily attached to and detached from the tube fixing portion 300 in a state in which the hemostatic device 100 is attached to the right hand H1 of the patient. Therefore, the tube fixing portion 300 may be provided on the fixing member 120 for fixing the inflatable member 110, and may be provided on any one of the bands 140, 150, and 160.

As shown in FIG. 3, the tube fixing portion 300 is located in the first curved region 134a of the support member 130 and outside the inflatable member 110.

The hemostatic device 100 is attached such that the first curved region 134a of the support member 130 does not come into contact with a surface of the right hand H1 of the patient.

Therefore, the operator can hold the support member 130 of the hemostatic device 100 attached to the right hand H1 of the patient by pinching with two fingers when fixing the tube portion 183 to the tube fixing portion 300.

The operator can insert the tube portion 183 into the tube fixing portion 300 with one finger located on an outer surface 130b side of the support member 130, and absorb an external force applied to the tube portion 183 with the other finger located on an inner surface 130a side of the support member 130.

Accordingly, the operator can fix the tube portion 183 to the tube fixing portion 300 without applying an unintended external force to the support member 130.

Since the operator pinches and holds the support member 130 of the hemostatic device 100 attached to the right hand H1 of the patient when fixing the tube portion 183 to the tube fixing portion 300, the support member 130 can be reliably prevented from being inclined due to the external force applied to the tube portion 183. Therefore, in the inflatable member 100, when the operator inserts the tube portion 183 into the tube fixing portion 300 in a state in which the hemostatic device 100 is attached to the right hand H1 of the patient, it is possible to help prevent an external force from being unintentionally applied to the first puncture site p1, and/or to help prevent the hemostatic device 100 from shifting due to unintentional application of an external force to the inflatable member 110 caused by transmission of the external force to the support member 130.

As shown in FIG. 3, the tube fixing portion 300 is provided at a position facing the third band 160 with the inflatable member 110 interposed between the tube fixing portion 300 and the third band 160. As shown in FIGS. 3 and 4, the connection portion K between the inflatable member 110 and the tube portion 183 is disposed on a third band 160 side in view of convenience in operating the injection member 180 when the operator adjusts a fluid amount of the inflatable member 110.

Therefore, since the tube fixing portion 300 is provided at the position facing the third band 160, it is possible to reduce a remainder of the tube portion 183 that may be generated between the tube fixing portion 300 and the connection portion K of the tube portion 183 fixed to the tube fixing portion 300.

Accordingly, when the patient moves the right hand H1 or the like, an end portion of the tube portion 183 on a connector portion 181 side can be prevented from swinging, and an external force can be prevented from being unintentionally applied to the inflatable member 110.

In addition, when the tube portion 183 is fixed to the tube fixing portion 300, a radius of curvature formed by the tube portion 183 located between the connection portion K and the tube fixing portion 300 is increased, and thus the tube portion 183 can also be prevented from kinking.

Usage Example of Hemostatic Device

Next, a usage example of the hemostatic device 100 will be described with reference to FIGS. 12 to 16.

In the usage example, procedures for using the hemostatic device 100 when stopping bleeding at the first puncture site p1 formed in the right hand H1 of the patient will be described.

FIG. 12 shows a state in which the sheath tube of the introducer 200 is inserted into the first puncture site p1 and various procedures have been performed.

When attaching the hemostatic device 100 to the right hand H1 of the patient, the operator disposes the support member 130 to overlap a dorsal side of the right hand H1 of the patient as shown in FIG. 12. At this time, the operator can appropriately position the inflatable member 110 at the first puncture site p1 by disposing the marker 115 at the first puncture site p1 while visually checking a position of the marker 115 disposed on the inflatable member 110.

The operator may pull out a part of the sheath tube of the introducer 200 from the first puncture site p1 formed in the right hand H1 of the patient after finishing a procedure using the introducer 200 and before attaching the hemostatic device 100 to the right hand H1 of the patient.

For example, the operator can start an attachment operation of the hemostatic device 100 after pulling out the sheath tube, for example, by approximately 2 cm to 3 cm to a hand side of the operator in a state in which the sheath tube of the introducer 200 is indwelled in the blood vessel B.

As shown in FIGS. 12 and 13, the operator wraps the first band 140 and the second band 150 along the outer periphery of the right hand H1 of the patient. The operator can connect the first band 140 and the second band 150 via the fixing sites 171 and 174 by bringing the fourth fixing site 174 disposed on the inner surface of the second band 150 (see FIG. 2) into contact with the first fixing site 171 disposed on the outer surface of the first band 140 (see FIG. 1).

As shown in FIG. 14, the operator passes the third band 160 through the inter-finger portion fb located between the thumb and the forefinger of the right hand H1 of the patient, and disposes a part of the third band 160 on a palm side of the right hand H1 of the patient. At this time, the operator can connect the second band 150 and the third band 160 via the fixing sites 172 and 175 by bringing the fifth fixing site 175 disposed on the inner surface of the third band 160 (see FIG. 2) into contact with the second fixing site 172 disposed on the outer surface of the second band 150 (see FIG. 1).

The operator inflates the inflatable member 110 by injecting air into the inflatable member 110 in a state in which the syringe is connected to the connector portion 181.

Figure 15:
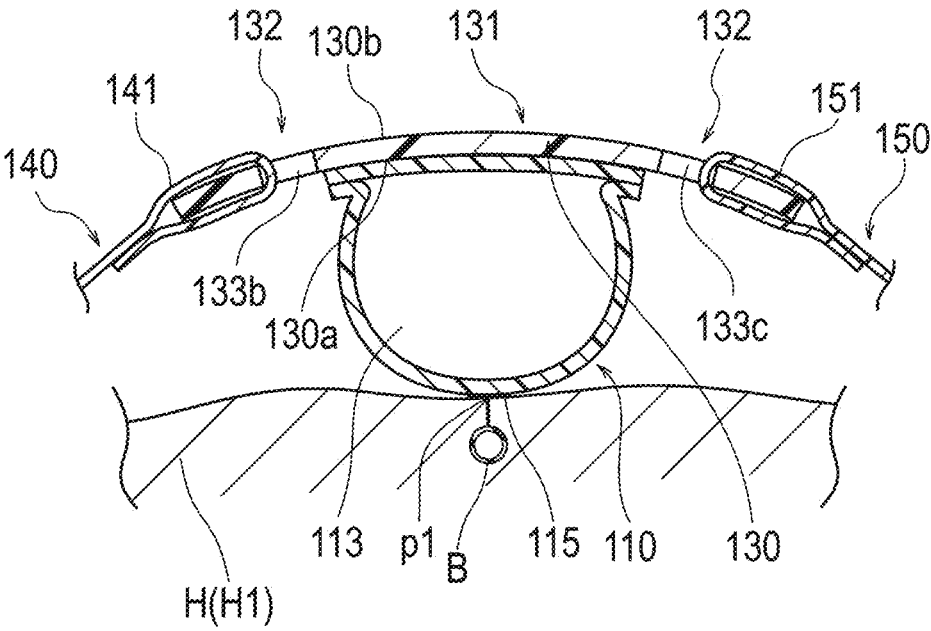
FIG. 15 is a cross-sectional view of a part taken along an arrow XVA-XVA shown in FIG. 14.
Figure 16:
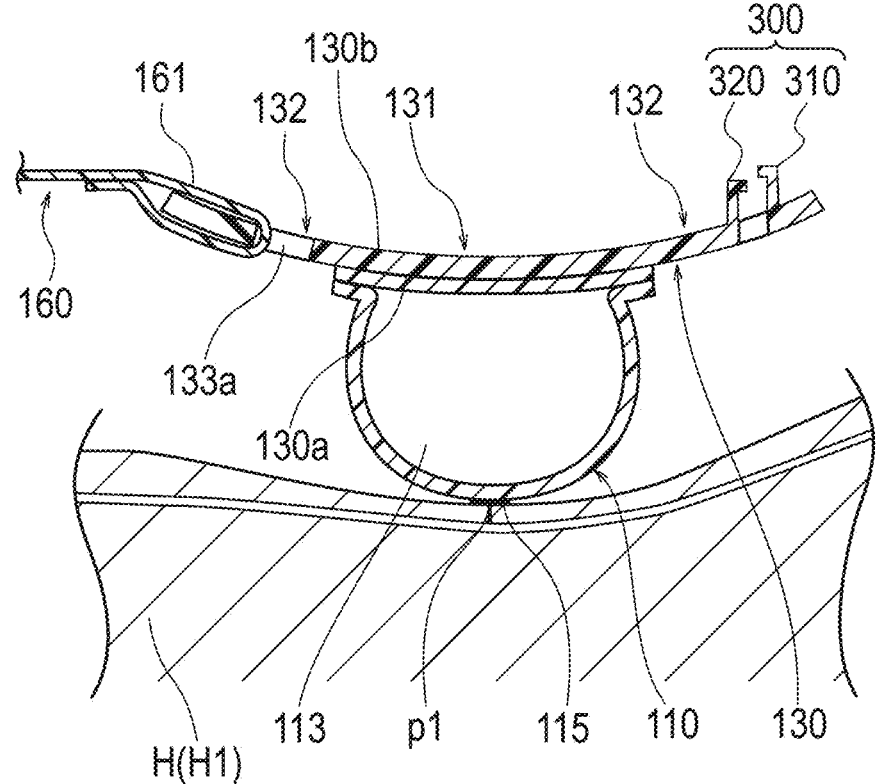
FIG. 16 is a cross-sectional view of a part taken along an arrow XVIA-XVIA shown in FIG. 14.

As shown in FIGS. 15 and 16, in the hemostatic device 100, when the inflatable member 110 is inflated, the inflatable member 110 applies a compressive force to the first puncture site p1 of the right hand H1 of the patient.

The operator fixes the tube portion 183 to the tube fixing portion 300 (see FIGS. 3 to 5).

The tube fixing portion 300 according to the present embodiment can reduce a force required for the operator to fix the tube portion 183 to the tube fixing portion 300.

The operator pinches and holds the support member 130 of the hemostatic device 100 attached to the right hand H1 of the patient when fixing the tube portion 183 to the tube fixing portion 300, whereby the support member 130 can be prevented from being inclined due to an external force applied to the tube portion 183 by the operator.

Therefore, in the hemostatic device 100, it is possible to prevent an external force from being unintentionally applied to the first puncture site p1, and/or to prevent the hemostatic device 100 from shifting due to unintentional application of an external force to the inflatable member 110.

According to the above procedures, the operator can stop bleeding at the first puncture site p1 formed in the right hand H1 of the patient using the hemostatic device 100.

In a case where the hemostatic device 100 stops bleeding at the second puncture site p2 formed in the right hand H1 of the patient, the operator slides the bands 140 and 150 about the center point R when wrapping the bands 140 and 150 around the right hand H1 of the patient.

The operator can stop bleeding at the second puncture site p2 formed in the right hand H1 of the patient by wrapping the slid bands 140 and 150 around the right hand H1 of the patient at a position closer to the forearm A (proximal side) than is the first puncture site p1.

As described above, the hemostatic device 100 according to the present embodiment includes: the inflatable member 110 configured to be capable of compressing a site where bleeding is to be stopped in a limb of a patient; the fixing member 120 configured to be capable of fixing the inflatable member 110 to the limb of the patient; the injection member 180 including the connector portion 181 configured to be capable of injecting a fluid for inflating the inflatable member 110 and the tube portion 183 connecting the connector portion 181 to the inner cavity 113 of the inflatable member 110; and the tube fixing portion 300 located on the fixing member 120 and configured to be capable of fixing the tube portion 183. The tube fixing portion 300 includes the first member 310, the second member 320 located closer to the inflatable member 110 than is the first member 310 and facing the first member 310, the slit portion 330 formed between the first member 310 and the second member 320 and configured to allow insertion of the tube portion 183, and the tube holding portion 340 surrounded by the first member 310, the second member 320, and the slit portion 330 and configured to hold the tube portion 183. The first member 310 includes the first portion 311, the first curved portion 312 curved toward the second member 320, and the first distal-end surface 313 located at a distal end of the first curved portion 312. The second member 320 includes the second portion 321, the second curved portion 322 curved toward the first member 310, and the second distal-end surface 323 located at a distal end of the second curved portion 322 and facing the first distal-end surface 313 across the slit portion 330. A part of the first member 310 is further away from the inflatable member 110 than is the second member 320 in a direction perpendicular to the virtual plane S defined by the slit portion 330. The first distal-end surface 313 includes the first region 313a not facing the second distal-end surface 323 across the slit portion 330 and the second region 313b facing the second distal-end surface 323 across the slit portion 330. The first curved portion 312 includes the first curved surface 312a curved toward the second member 320. The first curved surface 312a faces the second distal-end surface 323 across the tube holding portion 340.

According to the hemostatic device 100 configured as described above, by providing a height difference between the first member 310 and the second member 320, a region where the first distal-end surface 313 and the second distal-end surface 323 face each other across the slit portion 330 is reduced.

Therefore, the hemostatic device 100 can reduce a force required for the operator to insert the tube portion 183 into the tube fixing portion 300 in a state of being attached to the right hand H1 of the patient.

The first curved surface 312a is formed at a position facing the second distal-end surface 323 across the tube holding portion 340.

Therefore, in the hemostatic device 100, when the operator separates the tube portion 183 from the tube fixing portion 300 (removes the tube portion 183 from the tube fixing portion 300), the tube portion 183 can be moved from the tube holding portion 340 toward the slit portion 330 with the first curved surface 312a as a guide surface.

Accordingly, the hemostatic device 100 can reduce a force required for the operator to remove the tube portion 183 from the tube fixing portion 300 in the state of being attached to the right hand H1 of the patient.

Therefore, in the hemostatic device 100, it is possible to prevent an external force from being unintentionally applied to the puncture sites p1 and p2, and/or to prevent the hemostatic device 100 from shifting due to unintentional application of an external force to the inflatable member 110.

The fixing member 120 includes the support member 130 to which the inflatable member 110 is fixed, and a band (bands 140, 150, and 160) that is connectable to the support member 130, the support member 130 is made of a material more rigid than a material forming the band, and the tube fixing portion 300 is made of a material more rigid than a material forming the tube portion 183, and is located on a surface (outer surface 130b) of the support member 130.

According to the hemostatic device 100 configured as described above, the operator can easily perform an operation of attaching the tube portion 183 to and detaching the tube portion 183 from the tube fixing portion 300 in a state in which the hemostatic device 100 is attached to the right hand H1 of the patient.

Since the tube fixing portion 300 is made of a more rigid material than the tube portion 183, the first portion 311 and the second member 320 are less likely to be deformed by an unintentionally applied force, and the tube portion 183 held by the tube fixing portion 300 can be prevented from being unintentionally removed from the tube fixing portion 300.

Since the tube fixing portion 300 is provided on the support member 130 made of a relatively rigid material, the hemostatic device 100 can be prevented from shifting due to unintentional application of the external force to the inflatable member 110 connected to the support member 130.

The support member 130 includes the first curved region 134a curved in a direction away from the inflatable member 110, and the tube fixing portion 300 is located in the first curved region 134a and outside the inflatable member 110.

The hemostatic device 100 configured as described above is attached such that the first curved region 134a of the support member 130 does not come into contact with a surface of the right hand H1 of the patient.

Therefore, the operator holds and pinches the support member 130 of the hemostatic device 100 attached to the right hand H1 of the patient when fixing the tube portion 183 to the tube fixing portion 300, whereby an external force applied to the tube portion 183 can be absorbed by fingers of the operator.

Accordingly, the operator can fix the tube portion 183 to the tube fixing portion 300 without applying an unintended external force to the support member 130.

Since the operator holds and pinches the support member 130 of the hemostatic device 100 attached to the right hand H1 of the patient when fixing the tube portion 183 to the tube fixing portion 300, the support member 130 can be more reliably prevented from being inclined due to the external force applied to the tube portion 183 by the operator.

Therefore, in the inflatable member 100, when the operator inserts the tube portion 183 into the tube fixing portion 300 in a state in which the hemostatic device 100 is attached to the right hand H1 of the patient, it is possible to prevent an external force from being unintentionally applied to the puncture sites p1 and p2, and/or to prevent the hemostatic device 100 from shifting due to unintentional application of an external force to the inflatable member 110 caused by transmission of the external force to the support member 130.

The band includes the first band 140 extending from the support member 130 in a first direction, the second band 150 extending from the support member 130 in a second direction different from the first direction, and the third band 160 configured to be disposed between fingers of the patient and extending from the support member 130 in a third direction different from the first direction and the second direction. The connection portion K between the inflatable member 110 and the tube portion 183 is located on a third band 160 side. The tube fixing portion 300 is located on a surface (outer surface 130b) of the support member 130 facing the third band 160 with the inflatable member 110 interposed between tube fixing portion 300 and the third band 160.

According to the hemostatic device 100 configured as described above, it is possible to reduce a remainder of the tube portion 183 that may be generated between the tube fixing portion 300 and the connection portion K of the tube portion 183 fixed to the tube fixing portion 300.

In addition, when the tube portion 183 is fixed to the tube fixing portion 300, the tube portion 183 can be prevented from kinking between the connection portion K and the tube fixing portion 300.

The length X3 of the second region 313b of the first distal-end surface 313 is less than the radius r1 of the tube portion 183.

According to the hemostatic device 100 configured as described above, when the operator inserts the tube portion 183 into the tube fixing portion 300, the hemostatic device 100 can reduce an amount of work required for the operator to move the tube portion 183 from the slit portion 330 toward the tube holding portion 340.

Therefore, the hemostatic device 100 can reduce a force with which the operator pushes the tube portion 183 from the slit portion 330 toward the tube holding portion 340, and the operator can easily insert the tube portion 183 into the tube fixing portion 300.

Accordingly, in the hemostatic device 100, it is possible to prevent an external force from being unintentionally applied to the puncture sites p1 and p2, and/or to prevent the hemostatic device 100 from shifting due to unintentional application of an external force to the inflatable member 110.

The second distal-end surface 323 includes the curved surface portion 323c at a position facing the first distal-end surface 313 across the slit portion 330.

According to the hemostatic device 100 configured as described above, the hemostatic device 100 guides a moving direction of the tube portion 183 to the curved surface portion 323c when the operator inserts the tube portion 183 into the tube fixing portion 300, and facilitates the tube portion 183 held by the tube holding portion 340 to be directed to the slit portion 330. Therefore, the hemostatic device 100 can reduce a force required for the operator to insert the tube portion 183 into the tube fixing portion 300 in a state of being attached to the right hand H1 of the patient.

Accordingly, in the hemostatic device 100, it is possible to prevent an external force from being unintentionally applied to the puncture sites p1 and p2, and/or to prevent the hemostatic device 100 from shifting due to unintentional application of an external force to the inflatable member 110.

Next, a modification of the hemostatic device according to the disclosure will be described.

In the description of the modification, the description of members, procedures for using the hemostatic device, and the like already described in the description of the above embodiment will be appropriately omitted.

In addition, contents that are not particularly described in each modification may be the same as those of the above embodiment.

Modification

Figure 17:
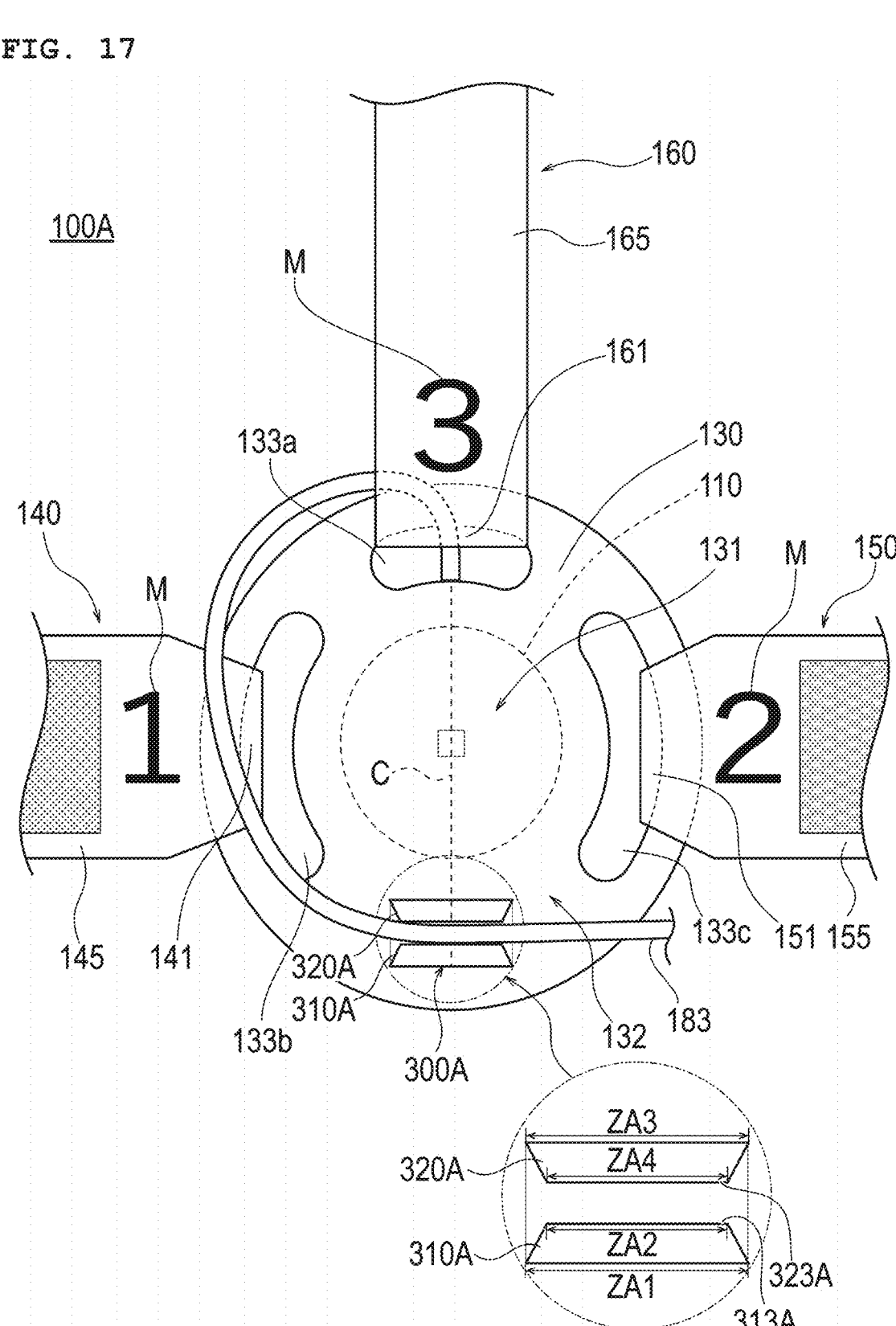
FIG. 17 is an enlarged plan view of a part of the hemostatic device according to Modification 1.

FIG. 17 is an enlarged view of a part of a hemostatic device 100A according to a modification.

As shown in FIG. 17, a tube fixing portion 300A of the hemostatic device 100A according to the modification includes a first member 310A and a second member 320A.

As shown in the enlarged view of the tube fixing portion 300A in FIG. 17, a width ZA2 of a first distal-end surface 313A is less than a width ZA1 of a first portion, and a width ZA4 of a second distal-end surface 323A is less than a width ZA3 of a second portion.

According to the hemostatic device 100A configured as described above, it is possible to reduce widths of the first distal-end surface 313A and the second distal-end surface 323A defining the slit portion 330 while increasing an area for disposing the tube fixing portion 300A to the support member 130.

Therefore, the hemostatic device 100A can help ensure a strength of the tube fixing portion 300A, and reduce a force required for the operator to attach the tube portion 183 to and detach the tube portion 183 from the tube fixing portion 300A in a state of being attached to the right hand H1 of the patient.

Therefore, in the hemostatic device 100A, it is possible to prevent an external force from being unintentionally applied to the puncture sites p1 and p2, and/or to prevent the hemostatic device 100 from shifting due to unintentional application of an external force to the inflatable member 110. In addition, the hemostatic device 100A can also increase the strength of the tube fixing portion 300A.

The hemostatic device according to the disclosure has been described above through the present embodiment, but the disclosure is not limited to the contents described in the specification, and can be appropriately changed based on the description of the claims.

The hemostatic device for stopping bleeding at the puncture site formed on the dorsal side of the right hand and the puncture site formed in the forearm has been exemplified in the description of the present embodiment. However, the hemostatic device may stop bleeding at a puncture site formed on a dorsal side of a left hand, a puncture site formed in a palm of any one of left and right hands, a puncture site formed in a foot of the patient (for example, dorsum or sole), or the like.

The shape, the dimension, and the like of each part of the hemostatic device are not particularly limited as long as the inflatable member can be disposed at a site where bleeding is to be stopped, and can be appropriately changed.

The detailed description above describes embodiments of a hemostatic device. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A hemostatic device comprising:

an inflatable member configured to compress a site where bleeding is to be stopped in a limb of a patient;

a fixing member configured to fix the inflatable member to the limb of the patient;

an injection member including a connector portion configured to inject a fluid for inflating the inflatable member, and a tube portion configured to connect the connector portion to an inner cavity of the inflatable member;

a tube fixing portion located on the fixing member and configured to secure the tube portion, the tube fixing portion includes a first member, a second member located closer to the inflatable member than is the first member and facing the first member, a slit portion formed between the first member and the second member and configured to allow insertion of the tube portion, and a tube holding portion surrounded by the first member, the second member, and the slit portion and configured to hold the tube portion;

the first member includes a first portion, a first curved portion curved toward the second member, and a first distal-end surface located at a distal end of the first curved portion;

the second member includes a second portion, a second curved portion curved toward the first member, and a second distal-end surface located at a distal end of the second curved portion and facing the first distal-end surface across the slit portion;

a part of the first member is further away from the inflatable member than the second member in a direction perpendicular to a virtual plane defined by the slit portion;

the first distal-end surface includes a first region not facing the second distal-end surface across the slit portion and a second region facing the second distal-end surface across the slit portion;

the first curved portion has a first curved surface curved toward the second member; and the first curved surface faces the second distal-end surface across the tube holding portion.

2. The hemostatic device according to claim 1, wherein a length of the second region of the first distal-end surface is less than a radius of the tube portion.

3. The hemostatic device according to claim 1, wherein the second distal-end surface includes a curved surface portion at a position facing the first distal-end surface across the slit portion.

4. The hemostatic device according to claim 1, wherein a width of the first distal-end surface is less than a width of the first portion; and a width of the second distal-end surface is less than a width of the second portion.

5. The hemostatic device according to claim 1, wherein the fixing member includes a support member to which the inflatable member is fixed, and a band configured to be connected to the support member;

the support member is made of a material more rigid than a material forming the band; and the tube fixing portion is made of a material more rigid than a material forming the tube portion, and the tube fixing portion is located on a surface of the support member.

6. The hemostatic device according to claim 5, wherein the support member includes a curved region curved in a direction away from the inflatable member; and the tube fixing portion is located in the curved region and outside the inflatable member.

7. The hemostatic device according to claim 5, wherein the band includes a first band extending from the support member in a first direction, a second band extending from the support member in a second direction different from the first direction, and a third band configured to be disposed between fingers of the patient and extending from the support member in a third direction different from the first direction and the second direction;

a connection portion between the inflatable member and the tube portion is located on a third band side; and the tube fixing portion is located on a surface of the support member facing the third band with the inflatable member interposed therebetween.

8. A tube fixing portion that is provided on a fixing member configured to fix an inflatable member of a hemostatic device to a patient, the tube fixing portion comprising:

a first member, a second member located closer to the inflatable member than the first member and facing the first member;

a slit portion formed between the first member and the second member and configured to allow insertion of a tube portion configured to be connected to an inner cavity of the inflatable member;

a tube holding portion surrounded by the first member, the second member, and the slit portion and configured to hold the tube portion;

the first member includes a first portion, a first curved portion curved toward the second member, and a first distal-end surface located at a distal end of the first curved portion;

the second member includes a second portion, a second curved portion curved toward the first member, and a second distal-end surface located at a distal end of the second curved portion and facing the first distal-end surface across the slit portion; and wherein the first distal-end surface includes a first region not facing the second distal-end surface across the slit portion and a second region facing the second distal-end surface across the slit portion.

9. The tube fixing portion according to claim 8, further comprising:

an injection member including a connector configured to inject a fluid into the inflatable member, and the tube portion configured to connect the connector to an inner cavity of the inflatable member.

10. The tube fixing portion according to claim 8, further comprising:

the inflatable member configured to compress a site where bleeding is to be stopped in a limb of the patient; and the fixing member configured to fix the inflatable member to the limb of the patient.

11. The tube fixing portion according to claim 8, wherein a width of the first distal-end surface is less than a width of the first portion; and a width of the second distal-end surface is less than a width of the second portion.

12. The tube fixing portion according to claim 8, further comprising:

a part of the first member is further away from the inflatable member than is the second member in a direction perpendicular to a virtual plane defined by the slit portion;

the first curved portion has a first curved surface curved toward the second member; and the first curved surface faces the second distal-end surface across the tube holding portion.

13. The tube fixing portion according to claim 12, wherein the tube fixing portion is made of a material more rigid than a material forming the tube portion, and the tube fixing portion is located on a surface of a support member of the fixing member to which the inflatable member is fixed.

14. The tube fixing portion according to claim 12, further comprising:

a length of the second region of the first distal-end surface is less than a radius of the tube portion.

15. The tube fixing portion according to claim 12, wherein the second distal-end surface includes a curved surface portion at a position facing the first distal-end surface across the slit portion.

16. The tube fixing portion according to claim 8, further comprising:

the fixing member includes a support member to which the inflatable member is fixed, and a band connectable to the support member; and the support member is made of a material more rigid than a material forming the band, the band being configured to be connected to the support member.

17. The tube fixing portion according to claim 16, wherein the support member includes a curved region curved in a direction away from the inflatable member, and the tube fixing portion is located in the curved region and outside the inflatable member.

18. A tube fixing portion, that is provided on a fixing member configured to fix an inflatable member of a hemostatic device to a patient, the tube fixing portion comprising:

a first member, a second member located closer to the inflatable member than the first member and facing the first member;

a slit portion formed between the first member and the second member and configured to allow insertion of a tube portion configured to be connected to an inner cavity of the inflatable member;

a tube holding portion surrounded by the first member, the second member, and the slit portion and configured to hold the tube portion;

the first member includes a first portion, a first curved portion curved toward the second member, and a first distal-end surface located at a distal end of the first curved portion;

the second member includes a second portion, a second curved portion curved toward the first member, and a second distal-end surface located at a distal end of the second curved portion and facing the first distal-end surface across the slit portion;

the fixing member includes a support member to which the inflatable member is fixed, and a band connectable to the support member;

the support member is made of a material more rigid than a material forming the band, the band being configured to be connected to the support member;

wherein the band includes a first band extending from the support member in a first direction, a second band extending from the support member in a second direction different from the first direction, and a third band configured to be disposed between fingers of the patient and extending from the support member in a third direction different from the first direction and the second direction;

a connection portion between the inflatable member and the tube portion is located on a third band side; and the tube fixing portion is located on a surface of the support member facing the third band with the inflatable member interposed therebetween.

19. A method for attaching a hemostatic device to a site where bleeding is to be stopped in a limb of a patient, the method comprising:

positioning an inflatable member fixed on a support member of the hemostatic device over the site to where the bleeding is to be stopped in the limb of the patient;

securing the inflatable member of the hemostatic device to the limb of the patient with a plurality of bands connected to the support member; and fixing a tube portion of an injection member to the support member using a tube fixing portion located on the support member and configured to fix the tube portion, the tube fixing portion including a first member, a second member located closer to the inflatable member than is the first member and facing the first member, a slit portion formed between the first member and the second member and configured to allow insertion of the tube portion, and a tube holding portion surrounded by the first member, the second member, and the slit portion and configured to hold the tube portion, the first member includes a first portion, a first curved portion curved toward the second member, and a first distal-end surface located at a distal end of the first curved portion, the second member includes a second portion, a second curved portion curved toward the first member, and a second distal-end surface located at a distal end of the second curved portion and facing the first distal-end surface across the slit portion, a part of the first member is further away from the inflatable member than is the second member in a direction perpendicular to a virtual plane defined by the slit portion, the first distal-end surface includes a first region not facing the second distal-end surface across the slit portion and a second region facing the second distal-end surface across the slit portion.

20. The method according to claim 19, wherein the first curved portion has a first curved surface curved toward the second member, and the first curved surface faces the second distal-end surface across the tube holding portion, and the method further comprises:

injecting a fluid into an inner cavity of the inflatable member; and after the injection of the fluid into the inner cavity of the inflatable member, performing the fixing of the tube portion to the support member using the tube fixing portion.

* * * * *